US007799003B2

(12) United States Patent
Johnson et al.

(10) Patent No.: US 7,799,003 B2
(45) Date of Patent: *Sep. 21, 2010

(54) EMERGENCY EYE WASH SYSTEM

(75) Inventors: Robert James Johnson, Katy, TX (US); David G. Key, Houston, TX (US); Kenneth J. Buras, Jr., Houston, TX (US); Troy A. Della Fiora, Spring, TX (US); Jim R. Dulaney, Euless, TX (US)

(73) Assignee: ENCON Safety Products, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/838,535

(22) Filed: Aug. 14, 2007

(65) Prior Publication Data

US 2008/0167632 A1 Jul. 10, 2008

Related U.S. Application Data

(62) Division of application No. 10/816,283, filed on Apr. 1, 2004, now Pat. No. 7,254,848.

(51) Int. Cl.
*A61M 35/00* (2006.01)
*A61H 35/02* (2006.01)

(52) U.S. Cl. .............................. 604/294; 4/620; 222/80

(58) Field of Classification Search ................. 604/294, 604/296–297, 300; 4/620
See application file for complete search history.

(56) References Cited

U.S. PATENT DOCUMENTS 2,168,270 A * 8/1939 Paisley et al. ............... 604/405
2,410,546 A * 11/1946 McCabe ..................... 251/157
2,416,391 A * 2/1947 Hixson ....................... 604/405
2,552,155 A * 5/1951 Danielson .................... 222/81
2,910,064 A * 10/1959 Brangaitis ................... 604/301
2,986,142 A * 5/1961 Bieberdorf et al. .......... 604/262
4,012,798 A * 3/1977 Liautaud ........................ 4/620
4,232,671 A * 11/1980 Crump ....................... 604/294
4,363,146 A * 12/1982 Liautaud ........................ 4/620
4,527,716 A * 7/1985 Haas et al. ................. 222/83.5
4,734,091 A * 3/1988 Boyle et al. ................. 604/521
4,784,652 A * 11/1988 Wikstrom ................... 604/295
4,881,283 A * 11/1989 Liautaud ........................ 4/620
4,939,800 A * 7/1990 Fiorentino et al. ............. 4/620

(Continued)

FOREIGN PATENT DOCUMENTS

FR 2625098 * 6/1989

(Continued)

*Primary Examiner*—Tatyana Zalukaeva
*Assistant Examiner*—Paula L Craig
(74) *Attorney, Agent, or Firm*—Moore & Van Allen PLLC; Michael G. Johnston

(57) ABSTRACT

An emergency eye wash system having a support panel and a pair of brackets for holding two bag assemblies containing sterile and sealed eye wash solution. The bag assemblies are connected by hoses to a pair of nozzles mounted on a pivotal tray assembly. When the system is dormant, the tray assembly is in a vertical closed position. When there is an emergency, a user pulls on a pivotal handle to puncture membranes in the hoses and to lower the tray assembly to cause flow from the bags to the nozzles to the user's face.

9 Claims, 20 Drawing Sheets

U.S. PATENT DOCUMENTS 4,976,379 A * 12/1990 Sloan .......................... 222/83
5,157,798 A * 10/1992 Van Kammen ................. 4/620
5,171,307 A * 12/1992 Sanning ...................... 604/327
5,320,615 A * 6/1994 Van Keuren ................ 604/297
5,334,180 A * 8/1994 Adolf et al. ................. 604/411
5,381,567 A * 1/1995 Tanner et al. .................. 4/620
5,391,163 A * 2/1995 Christine et al. ............ 604/408
5,695,124 A * 12/1997 Demeny et al. ............. 239/327
5,732,853 A * 3/1998 Ganzeboom et al. .......... 222/82
5,774,908 A * 7/1998 Hall .............................. 4/617
5,931,820 A * 8/1999 Morse ........................ 604/533
6,070,279 A * 6/2000 Lundstedt ...................... 4/620
6,098,844 A * 8/2000 Nicolle ........................ 222/80
6,296,626 B1 * 10/2001 Stein .......................... 604/294
6,554,164 B1 * 4/2003 Jones ......................... 222/105
7,011,652 B1 * 3/2006 Berke et al. ................. 604/300
7,254,848 B2 * 8/2007 Johnson et al. ................ 4/620
7,354,426 B2 * 4/2008 Young ........................ 604/403
7,490,741 B2 * 2/2009 Rochefort et al. ........ 222/181.3
2002/0107492 A1 * 8/2002 Brach et al. ................. 604/296
2004/0089672 A1 * 5/2004 Crosland et al. ............ 222/105
2005/0054992 A1 * 3/2005 Madritsch et al. ........... 604/294
2005/0077318 A1 * 4/2005 Macler et al. ................. 222/81
2006/0011657 A1 * 1/2006 Wright ....................... 222/212
2007/0271694 A1 * 11/2007 Johnson et al. ................ 4/620
2009/0007327 A1 * 1/2009 Johnson et al. ................ 4/620

FOREIGN PATENT DOCUMENTS

WO WO8702237 * 4/1987
WO WO03065967 * 8/2003

* cited by examiner

FIG. 9
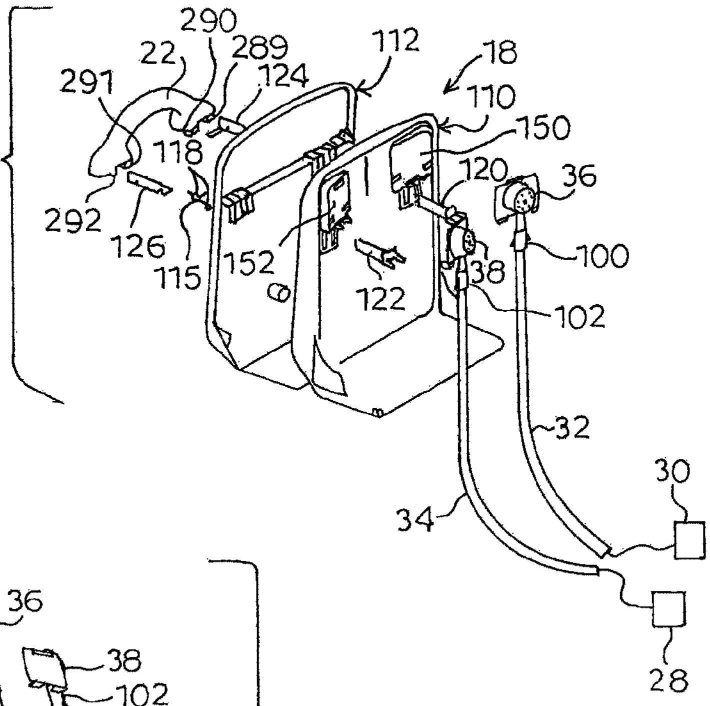
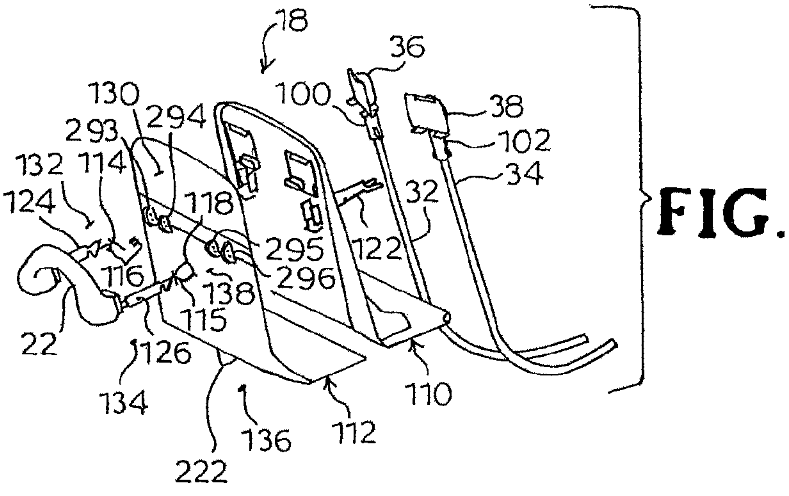
FIG. 10
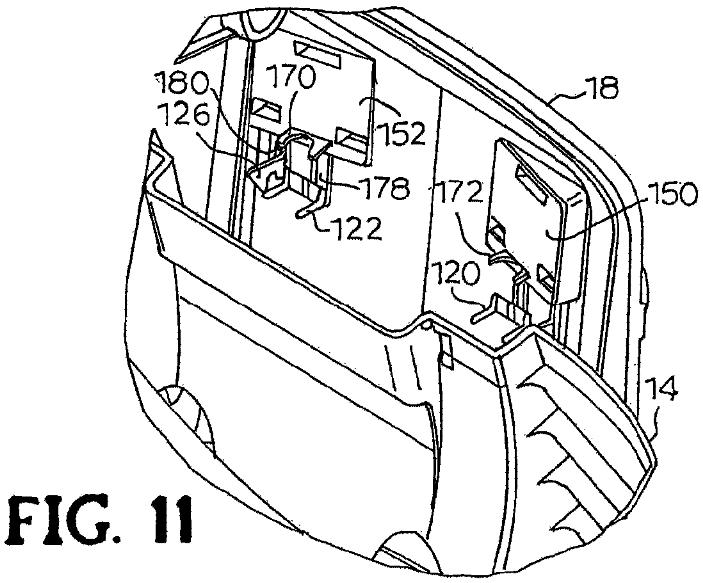
FIG. 11

EMERGENCY EYE WASH SYSTEM

CROSS REFERENCE TO PRIORITY APPLICATIONS

This application is a divisional application of U.S. patent application Ser. No. 10/816,283, filed Apr. 1, 2004, now U.S. Pat. No. 7,254,848, issued Aug. 14, 2007, the contents of which are incorporated herein by reference.

STATEMENT REGARDING FEDERALLY SPONSORED RESEARCH

Not applicable.

BACKGROUND OF THE INVENTION

1. Field of the Invention

The present invention relates to an emergency eye wash system and more particularly to an emergency eye wash system which is simply constructed, compact and reliable.

2. Description of the Related Art

Emergency eye wash systems are often present in industrial plant settings, industry and academic laboratories and in commercial environments where researchers, students, customers and workers may be accidentally exposed to dangerous conditions and materials.

The Occupational Safety And Health Administration has ruled that eye wash fountains are mandatory at specified industrial work stations. The American National Standards Institute has issued standards for portable eye wash fountains relating to flushing periods and rate of flow. The present requirements are that the eye wash nozzles in a portable eye wash fountain should deliver no less than an aggregate of one and one-half liters per minute (approximately 0.4 gallons per minute) of eye wash fluid during a fifteen minute period.

A number of eye wash devices and liquid carrying bags have been patented over the years as shown in the following U.S. Pat. Nos.: 4,012,798; 4,363,146; 4,526,793; 4,881,283; 4,939,800; 5,566,406; 5,695,124; 5,774,908; and 5,850,641. These devices, however, tend to be overly complicated, relatively expensive and not very reliable. Some of these devices also tend to be bulky.

It is also important that such emergency eye wash systems be readily accessible and easily and quickly operated. An emergency eye wash system must also operate effectively once activated even though the system sat dormant for a long time period.

What is described here is an emergency eye wash system including a housing having a movable tray, a source of eye wash fluid mounted in the housing, two eye spraying nozzles mounted on the tray, and a conduit connecting the nozzle and the fluid source, the conduit being slideable from a closed position to an open position whereby in the open position, eye washing fluid is able to flow from the fluid source to the nozzle.

There are a number of advantages, features and objects achieved with the present invention which are believed not to be available in earlier related devices. For example, the system disclosed here is simply constructed, reliable and relatively inexpensive. The system disclosed here also meets government regulations relating to flow rate, duration and shelf life. A further advantage of the disclosed system is that it is compact and easily mounted to a variety of structures so as to be readily accessible.

A complete understanding of the present invention and other objects, advantages and features thereof will be gained from a consideration of the present specification which provides a written description of the invention, and of the manner and process of making and using the invention, set forth in such full, clear, concise and exact terms as to enable any person skilled in the art to which it pertains, or with which it is most nearly connected, to make and use the same in compliance with Title 35 U.S.C. Section 112 (first paragraph). Furthermore, the following description of a preferred embodiment of the invention read in conjunction with the accompanying drawing provided herein represents an example of the invention which is described here in compliance with Title 35 U.S.C. section 112 (first paragraph), although the invention itself is defined in the Claims section attached hereto.

BRIEF DESCRIPTION OF THE SEVERAL VIEWS OF THE DRAWING

FIG. 9 is a rear looking, exploded isometric view of a tray assembly, nozzles and hoses as well as a diagrammatic representation of two bag assemblies.

FIG. 10 is a front looking, exploded isometric view of the tray assembly, nozzles and hoses.

FIG. 11 is an enlarged partial rear isometric view of the tray assembly and a front part of the housing.

DETAILED DESCRIPTION OF A PREFERRED EMBODIMENT OF THE INVENTION

Figure 1:
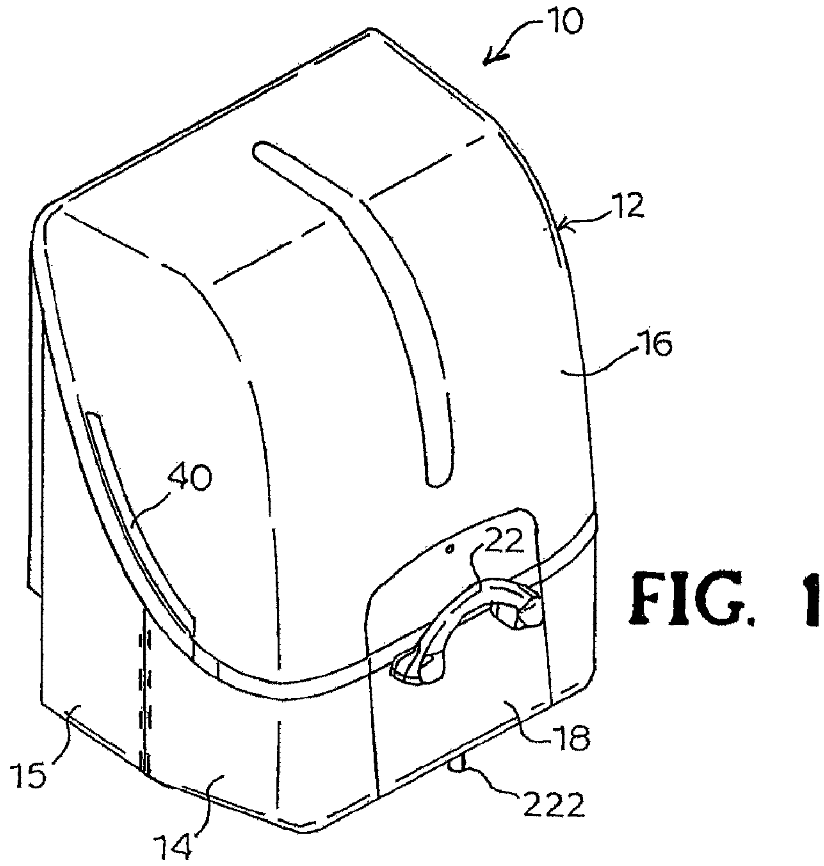
FIG. 1 is an isometric front view of an emergency eye wash system, in a closed position.
Figure 2:
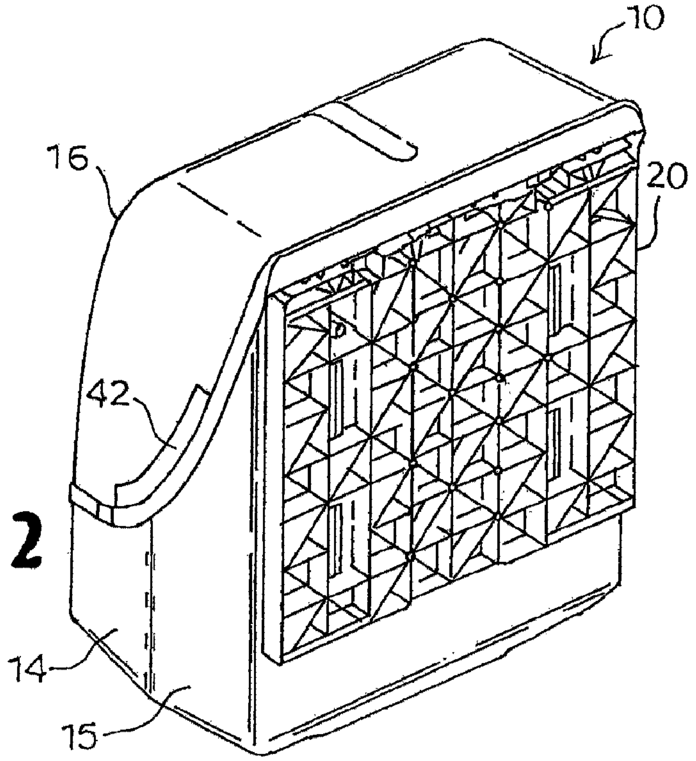
FIG. 2 is an isometric rear view of the emergency eye wash system.

While the present invention is open to various modifications and alternative constructions, the preferred embodiment illustrating the best mode contemplated by the inventors of carrying out their invention are shown in the various figures of the drawing and will be described herein in detail pursuant to Title 35 U.S.C. Section 112 (first paragraph). It is understood, however, that there is no intention to limit the invention to the particular embodiment, form or example which is disclosed here. On the contrary, the intention is to cover all modifications, equivalent structures and methods, and alternative constructions falling within the spirit and scope of the invention as expressed in the appended Claims section, pursuant to Title 35 U.S.C. section 112 (second paragraph).

Referring now to FIGS. 1-5, there is illustrated an emergency eye wash system 10 which includes a housing 12. The housing in turn includes a front part 14, a rear part 15, a lid, 16, a pivotal tray assembly 18 and a support structure in the form of a ribbed panel 20. The tray assembly includes a pivotal handle 22. The system also includes a pair of hanger brackets 24, 26 directly attached to the support panel 20 and a source of eye wash fluid in the form of two bag assemblies 28, 30 supported on the hanger brackets and positioned in the housing 12. Extending from the bottom of each bag assembly is a conduit in the form of a hose or tube 32, 34. The hoses 32, 34 are positioned along the tray assembly 18 and are connected to two eye spray nozzles 36, 38.

Figure 4:
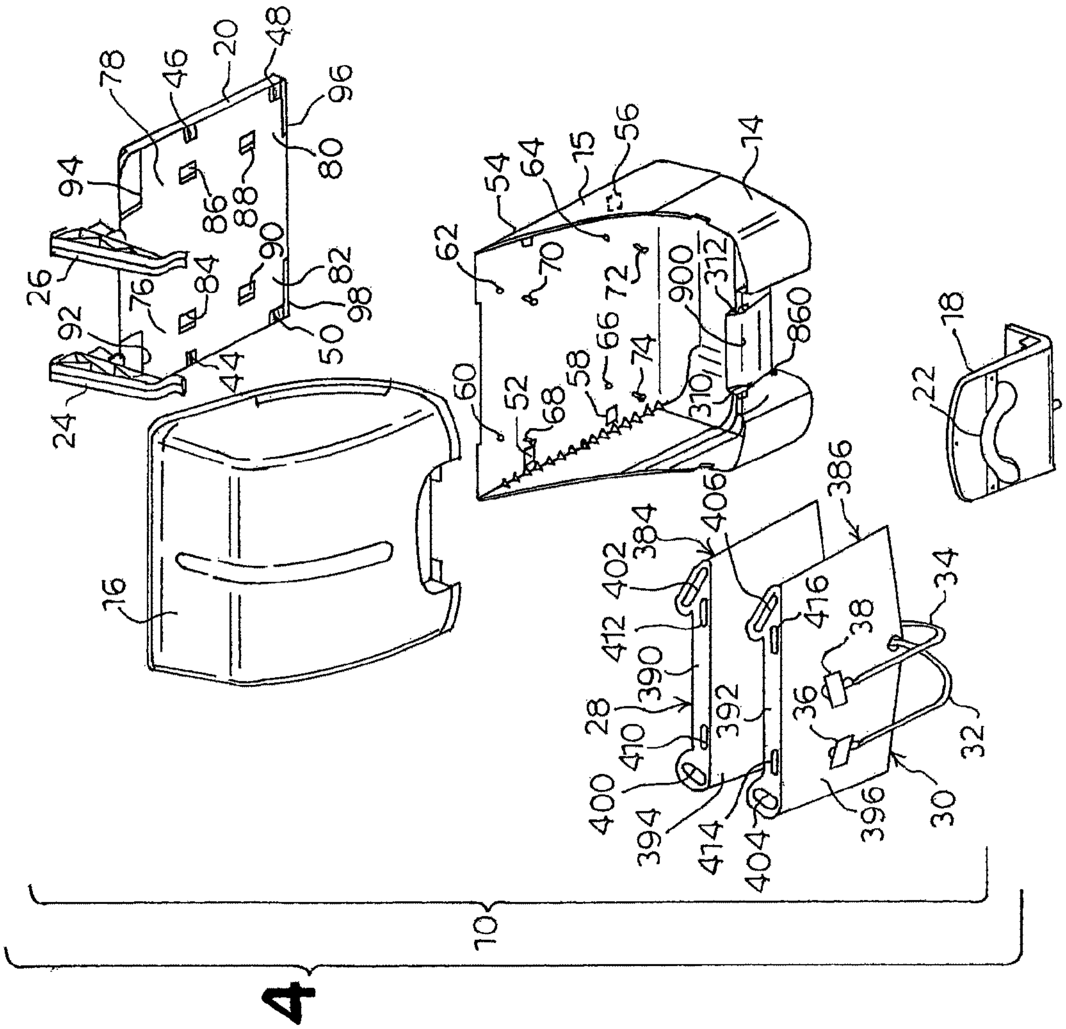
FIG. 4 is a downward looking, exploded isometric view of the emergency eye wash system shown in FIGS. 1-3.

The lid 16 features two acrylic inspection windows 40, 42. The lid 16 is removable to allow access to the bag assemblies 28, 30 and to the support panel 20 and the hanger brackets 24, 26. The support panel 20 includes four offset tabs 44, 46, 48, 50 as shown in FIG. 4. The rear housing part 15 includes four openings of 52, 54, 56, 58 to receive the tabs 44, 46, 48, 50 and thereby allow easy engagement between the rear housing part 15 and the support panel 20. The rear housing part also includes four screw receiving openings 60, 62, 64, 66 to receive screws 68, 70, 72, 74 for fastening the rear housing part to the support panel using screw receiving openings 76, 78, 80, 82 in the support panel 20.

The support panel also includes four openings 84, 86, 88, 90 which are capable of receiving attachment bands (not shown) and slot openings 92, 94, 96, 98 (which are configured to receive bolts or screws (not shown) to allow the support panel to attach to a variety of building structures. By attaching the support panel 20 to a building structure, the weight of the bag assemblies 28, 30, the hanger brackets 24, 26 and the support panel 20 are directly transmitted to the building structure rather than to the housing 12. This also allows the bag assemblies to hang freely. The housing itself, including the front part 14, the rear part 15 and the tray assembly 18 are all mounted to the support panel 20. Thus, all loads are carried by the support panel 20 and transmitted to a building support.

Figure 5:
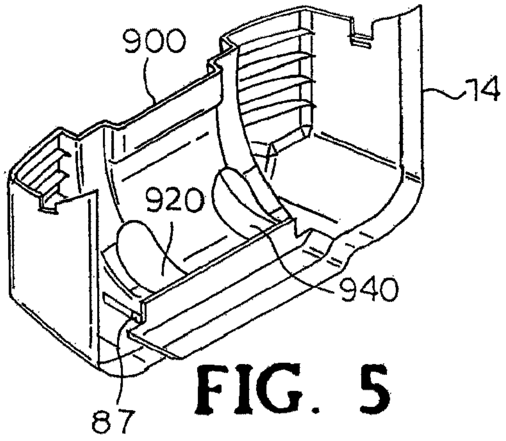
FIG. 5 is a rearward looking isometric view of a housing front part of the eye wash system housing.

The tray assembly 18 is pivotally connected to the housing front part 14 through openings 86, FIG. 4, and 87, FIG. 5. The tray assembly 18 is located in an indented central portion 90 of the housing front part 14. The indented portion also includes two access openings 92, 94 through which the nozzles and attached hoses pass after the two bag assemblies 28, 30 are hung onto the hanger brackets 24, 26. For purposes of orientation, the bags of the assemblies 28, 30 are considered "upstream" and the nozzles 36, 38 are considered "downstream" in relation to liquid flow from the bags to the nozzles. The housing front part 14 and rear part 15 are constructed to be engaged by any convenient technique, such as by bonding.

Figure 3:
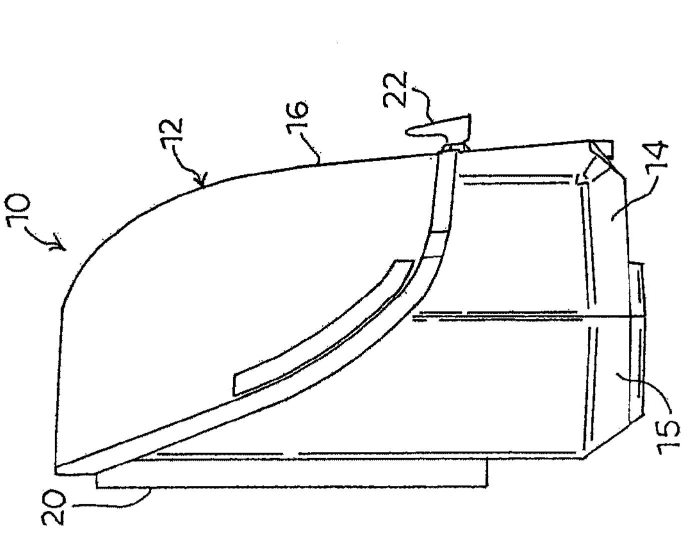
FIG. 3 is a side elevation view of the emergency eye wash system.
Figure 7:
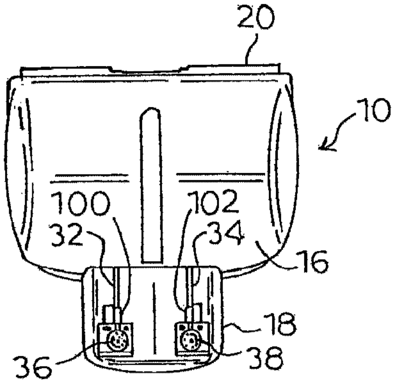
FIG. 7 is a top plan view of the emergency eye wash system shown in FIG. 6.
Figure 6:
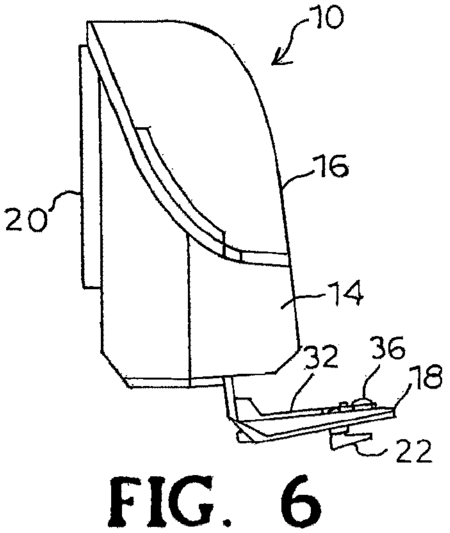
FIG. 6 is a side elevation view of the emergency eye wash system shown in an open position.
Figure 8:
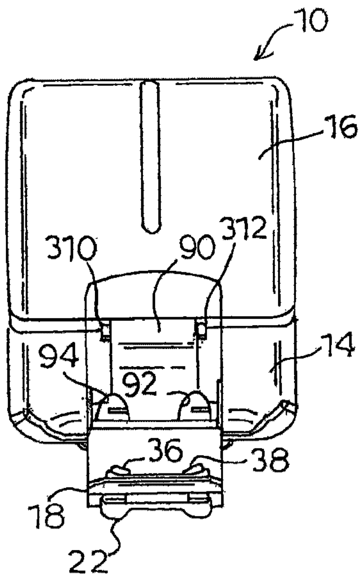
FIG. 8 is a front elevation view of the emergency eye wash system shown in FIGS. 6 and 7.
Figure 13:
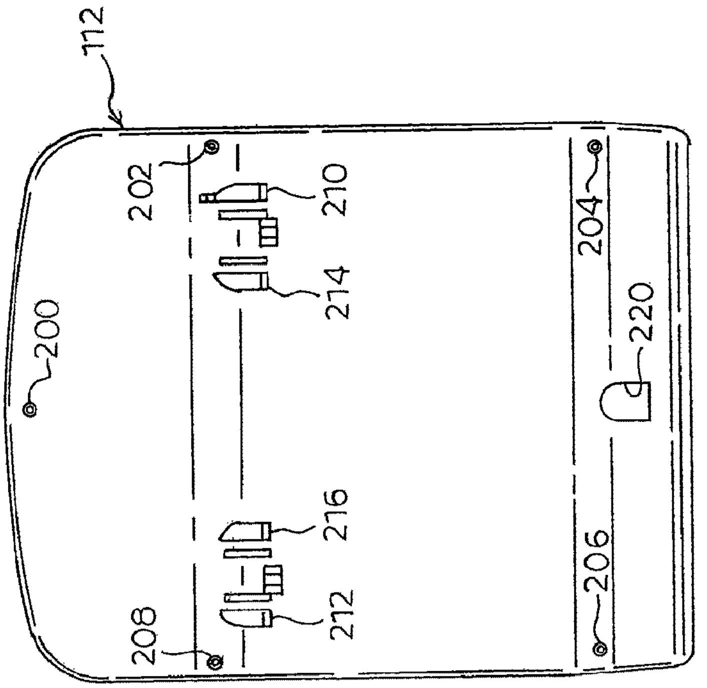
FIG. 13 is a view of the outer side of an outer tray part of the tray assembly.
Figure 12:
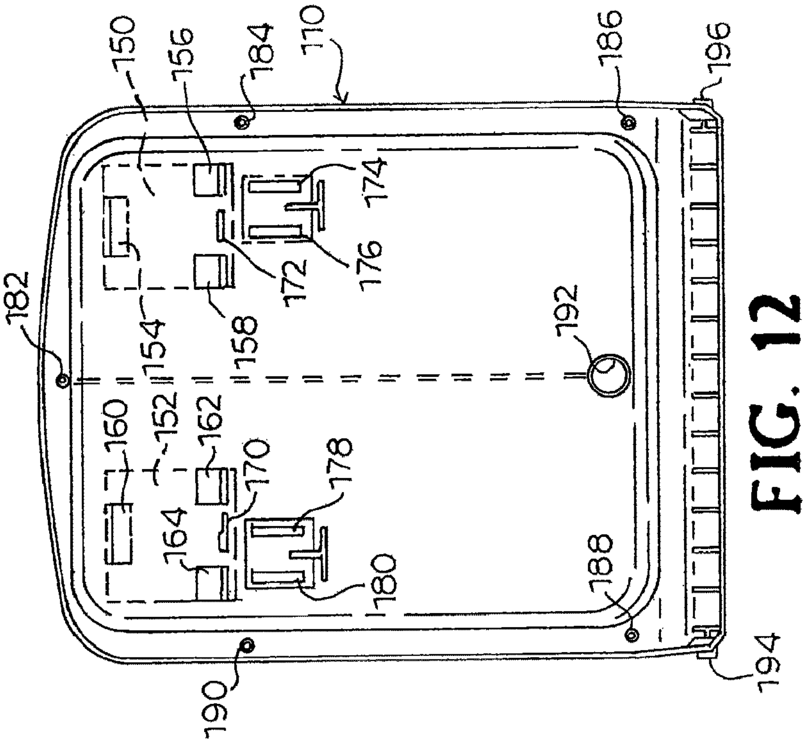
FIG. 12 is a view of the inner side of an inner tray part of the tray assembly.

In FIGS. 1 and 3, the tray assembly 18 is shown in a vertically oriented closed position and in FIGS. 6-8, in a horizontally oriented open position. When the emergency eye wash system is not in use, the tray assembly is in the closed position, however, in an emergency the tray assembly is in an operative, open position where it is generally horizontally disposed so that someone in need of an emergency eye wash can lower his/her head and locate his/her eyes within the spray pattern of an eye wash solution emanating from the two nozzles 36, 38.

The tray assembly is shown in an open position as it would appear during emergency operation in FIGS. 6-8. Shown is the already mentioned hoses 32, 34 connecting the solution containing bag assemblies 28, 30 and the nozzles 36, 38. In addition there is illustrated a pair of hose connector assemblies 100, 102.

The housing and handle may be made of any suitable material, such as acrylonitrilebutadiene-sytrene (ABS). The support panel and hanger brackets may be made of glass filled polycarbonate (PC). The tray parts may be made of ABS also. The hose may be made of medical grade PVC and, in a preferred embodiment of the present invention, have an inside diameter of about 0.250 inches and a length of about eighteen inches. It is noted that other suitable materials may be used.

Referring now to FIGS. 9-13, the tray assembly 18 is illustrated in more detail. The tray assembly includes an inner tray part 110, an outer tray part 112, the handle 22, stainless steel pivot pins 114, 115, two pairs of stainless steel torsion springs 116, 118, a pair of powder-coated steel pivotal forks 120, 122, a pair of powder-coated steel pivotal latches or lock arms 124, 126 and five fasteners 130, 132, 134, 136, 138 for connecting the inner and outer tray parts 110, 112. Additionally, the two tray parts 110, 112 are bonded together using a solvent that causes the plastic to melt together. This bonding creates a water-tight seal. Operative ends of the pivotal fork 120 and latch 124 are shown enlarged in FIG. 11. Illustrated in FIG. 9, in diagrammatic form, are the two bag assemblies 28, 30 and the two hoses 32, 34, as well as the two nozzles 36, 38 and the two hose connector assemblies 100, 102.

The inner tray 110 includes a pair of nozzle pads 150, 152 each with connector slots 154, 156, 158 and 160, 162, 164, clip removal prongs 170, 172, four through slots 174, 176 and 178, 180, where the inner two slots 176, 178 receive the pivotal forks 120, 122, and the outer two slots 174, 180 receive the pivotal latches 124, 126. Five screw receiving openings 182, 184, 186, 188, 190 are also formed in the inner tray part. The inner tray part 110 also includes a drain opening 192 and integral pivot pins 194, 196. The nozzle pads 150, 152 and prongs 170, 172 are shown more clearly in FIG. 11.

The outer tray part 112 also includes five screw receiving openings 200, 202, 204, 206, 208, a pair of outer slots 210, 212 for the pivotal latches 124, 126 and two inner slots 214, 216 for the two pivotal forks 120, 122. A central drain channel 220 is also provided. The channel 220 is aligned with the drain opening 192 of the inner tray part 110 and directs sprayed solution to an outer drain 222 shown in FIGS. 1 and 10.

Operation of the emergency eye wash system is simple, easily performed and very reliable. A user merely grips the handle 22 and pulls. This simple operation, a rotational motion, not only opens the tray assembly but moves it from a vertical closed position to a horizontal open position while at the same time opening the hose assembly to allow the flow of eye wash solution from the bag assemblies 28, 30 downstream through the hoses 32, 34 to the nozzles 36, 38.

Figure 14:
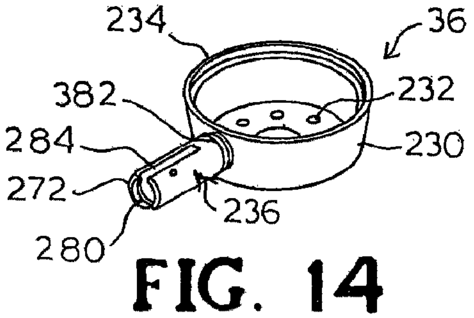
FIG. 14 is an enlarged isometric view of a nozzle.

The various elements in the flow path of the eye wash solution are illustrated in FIGS. 14-21. Referring first to FIG. 14, the nozzle 36 includes a cup portion 230 having perforations, such as eight conically shaped holes 232, a peripheral edge 234, and a stem 236. In a preferred embodiment, the illustrated eight hole nozzle 36 provides about 0.0127 square inches of open area through the holes.

Figure 15:
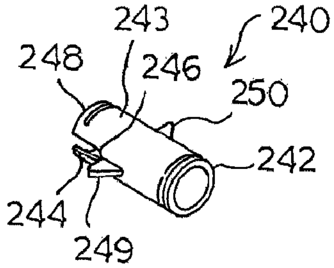
FIG. 15 is an enlarged upstream looking isometric view of a connector sleeve.
Figure 16:
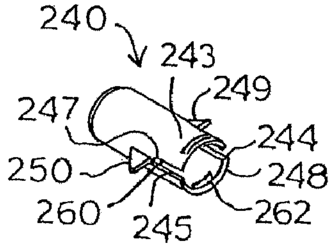
FIG. 16 is a downstream looking isometric view of the connector sleeve.
Figure 17:
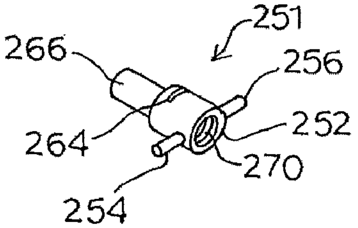
FIG. 17 is an upstream looking isometric view of a hose connector.
Figure 18:
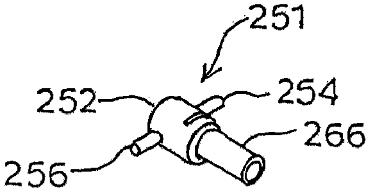
FIG. 18 is a downstream looking isometric view of the hose connector.

Positioned around the stem is a connector sleeve 240, FIGS. 15 and 16. The connector sleeve has a downstream end portion 242 which that fits around the stem 236 of the nozzle. Toward the upstream portion 243 of the connector sleeve are two longitudinally extending slots 244, 245, with slot ends 246, 247 and an upstream peripheral edge 248. Formed adjacent the slot ends are triangular flanges 249, 250. Fitted within the connector sleeve is a T-shaped hose connector 251, FIGS. 17 and 18. The hose connector includes a downstream portion 252 and two outwardly extending arms 254, 256. The downstream portion 252 of the hose connector is received in the upstream portion 243 of the connector sleeve until the hose connector abuts a shoulder 260, FIG. 16, in the connector sleeve 240. The arms 254 and 256 are received respectively in the two slots 244 and 245. A snap engagement between the connector sleeve and the hose connector is made when a projection 262 on the inner wall of the connector sleeve 240 "snaps" into a groove 264 of the hose connector 251. The hose connector also includes a smaller diameter upstream portion 266. Mounted in the downstream portion of the hose connector is a breakable membrane 270. The membrane is frangible, being made of an aluminum foil or foil/polymer laminate material and having a thickness of about 0.003 inches.

Figure 19:
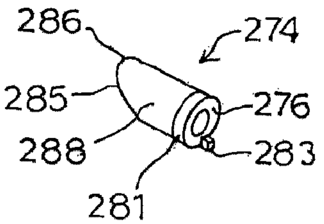
FIG. 19 is an upstream looking isometric view of a piercing element.
Figure 20:
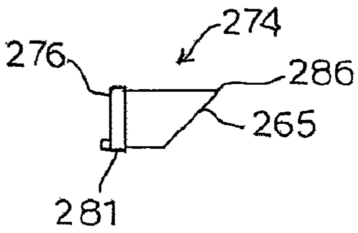
FIG. 20 is a side elevation view of the piercing element.
Figure 21:
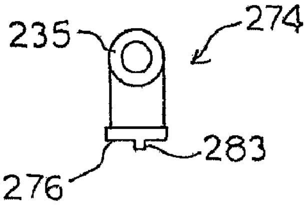
FIG. 21 is a bottom plan view of the piercing element.

Mounted at an upstream end portion 272 of the nozzle stem 236, FIG. 14, is a cylindrical piercing element 274, FIGS. 19-21. The piercing element has a downstream end portion 276 which is received in the upstream end portion 272 of the nozzle stem 236. These form an interference fit when an interior projection 280 in the nozzle stem 236 abuts a collar 281 of the downstream end portion 276 of the piercing element 274. The piercing element also includes a key 283 which is received in a slot 284 in the stem 236 of the nozzle. The piercing element has an upstream slanted end portion 285 resulting in the farthest upstream end 286 of the piercing element being relatively sharp.

Figure 22:
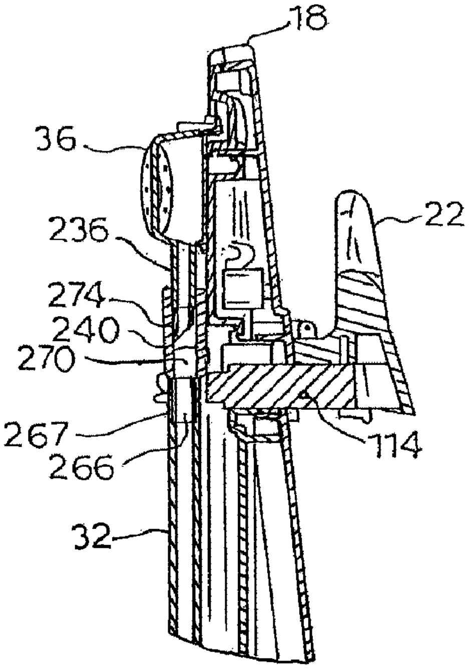
FIG. 22 is an enlarged sectional elevation view taken within the circle 22-22 of FIG. 3 showing the handle in a non-actuated position.
Figure 23:
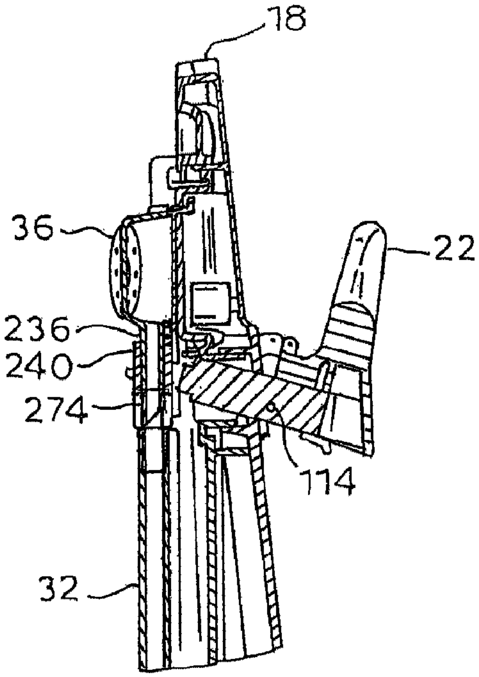
FIG. 23 is a sectional elevation view similar to that shown in FIG. 22 where the handle has been pivoted.

The operative alignment (moving in an upstream direction) of the nozzle stem 236, the piercing element 274, the connector sleeve 240, the hose connector 251 and the hose 32 are illustrated in FIGS. 22 and 23, where the upstream portion 266 of the hose connector is received by a downstream end portion 267 of the hose 32. When the tray assembly is in its vertical closed position, these aligned elements are shown in FIG. 22 where the membrane 270 blocks the flow of eye wash solution so that no solution reaches the nozzle cup portion 230. However, when the handle 22 of the tray assembly is pivoted through an arc of about 14 degrees and then 2 degrees beyond for a total of about 16 degrees, the handle and the aligned elements assume the positions shown in FIG. 23, where the connector sleeve 240, the hose connector 251 and the hose 32 have been shifted downstream pushing the membrane 270 against the piercing element 274 causing the membrane to be pierced and peeled back so as to be moved out of the flow path of the eye wash solution.

Movement of the connector sleeve, the hose connector and the hose downstream against the stationary nozzle and piercing element is caused by the forks 120, 122. The arms 254, 256 of the hose connector 251 are pushed against the ends 246, 247 of the slots 244, 245 so that the connector sleeve 240 slides downstream along the nozzle stem 236 toward the nozzle cup 230. The nozzle cup and the nozzle stem are stationary as is the piercing element 274. The downstream movement of the hose connector with the frangible membrane causes the membrane to be pierced by the sharp edge 286 of the piercing element 274 and for the membrane to be progressively sliced by the slanted surface 285 of the piercing element. As the membrane moves downstream, the severed portion of the membrane is being progressively laid back and progressively pushed toward an inner wall 287, FIG. 22, of the hose connector such that an outer cylindrical surface 288, FIG. 19, of the piercing element squeezes the cut membrane between itself and the inner wall of the hose connector. In this way, passageways between the eyewash solution in the bag assemblies 28, 30 and the nozzles 36, 38 are opened and cleared. The membrane is partially severed and moved out of the way so as not to interfere with the flow of eye wash solution and yet the membrane is also constrained so as not to be swept downstream and block the nozzle openings 232.

The handle 22 pivots about the pivot pins 114, 115, FIGS. 9 and 10, which are placed through flanges 289, 290, 291, 292, FIG. 9, on the handle and flanges 293, 294, 295, 296, FIG. 10, on the outer tray part 112. The pivoting movement of the handle is translated to the arms 254, 256 of the hose connector 251 by way of the pivotal forks 120, 122, FIGS. 9 and 10. The pivotal forks are also mounted to pivot on the pins 114, 115 and each fork has a handle engaging portion 297, FIGS. 24 and 25, a pivot opening 298, and a pair of fingers 299, 300. The fingers engage the arms 254, 256 of the hose connector 251, FIG. 17, where rotating motion of the pivotal fork translates to linear motion of the hose connector because the sliding engagement of the forks on the arms develops a component of force in a downstream direction.

Figure 24:
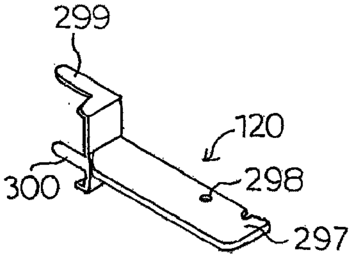
FIG. 24 is a forward looking isometric view of a pivotal fork.
Figure 25:
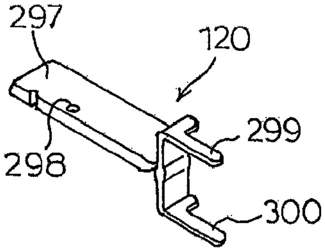
FIG. 25 is a rearward looking isometric view of the pivotal fork.
Figure 27:
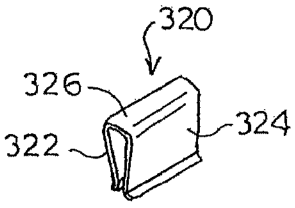
FIG. 27 is an isometric view of a latch clip.
Figure 26:
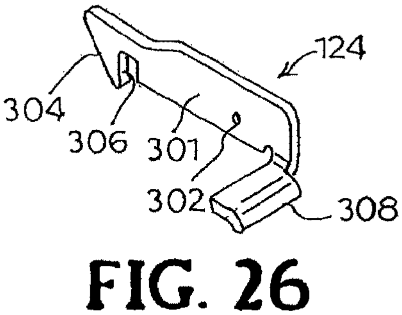
FIG. 26 is an isometric view of a pivotal latch.

Also pivotally mounted to the pins 114, 115 are the pivotal latches 124, 126. (A duplicate pivotal fork 122 and a mirror image pivotal latch 126 to those shown in FIGS. 24-26 are mounted to the pin 115.) Each pivotal latch includes a body portion 301, FIG. 26, a pivot hole 302 for receiving the pin, a latch head 304 having a slot 306 and a lateral tab 308. The two pivotal latches ensure that the tray assembly is maintained in the vertical close position by virtue of the heads, such as the head 304, extending through front openings 310, 312, FIGS. 4 and 8, in the indented portion 90 of the housing front part 14. To ensure a strong, robust engagement between the pivotal latch and the housing, a powder-coated steel latch clip 320, FIG. 27, is provided. The clip has opposed spring arms 322, 324 and a base 326. The spring arms fit over the wall of the housing front part leaving the base 326 in an upright position. The slot 306 of the pivotal latch fits over the base and adjacent portions of the spring arms so as to create a secure interference fit.

Figure 28:
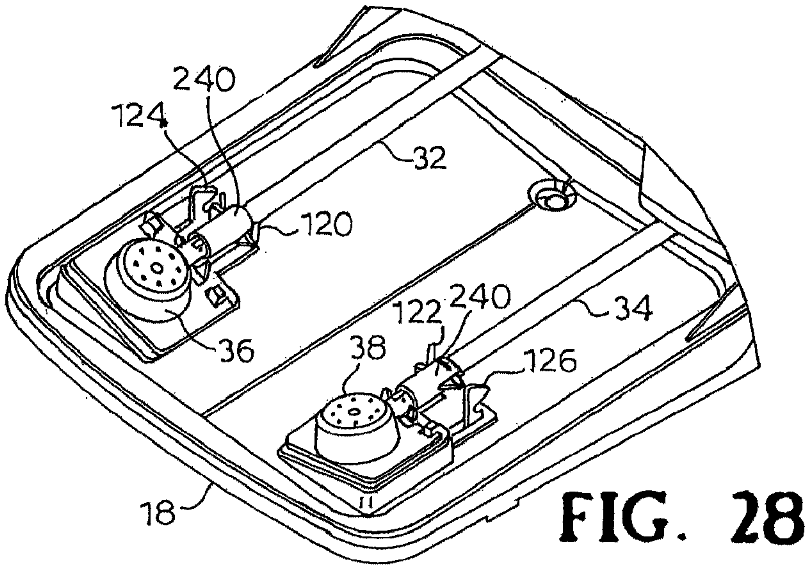
FIG. 28 is an isometric view of the tray assembly, the nozzle, the connector sleeve, the hose connector, the pivotal fork and the pivotal latch.

The forks 120, 122 and the connector sleeves 240 are shown in operative positions in FIG. 28. The latch 124 is shown engaged through the opening 310 with the clip 320 in FIG. 29.

Figure 30:
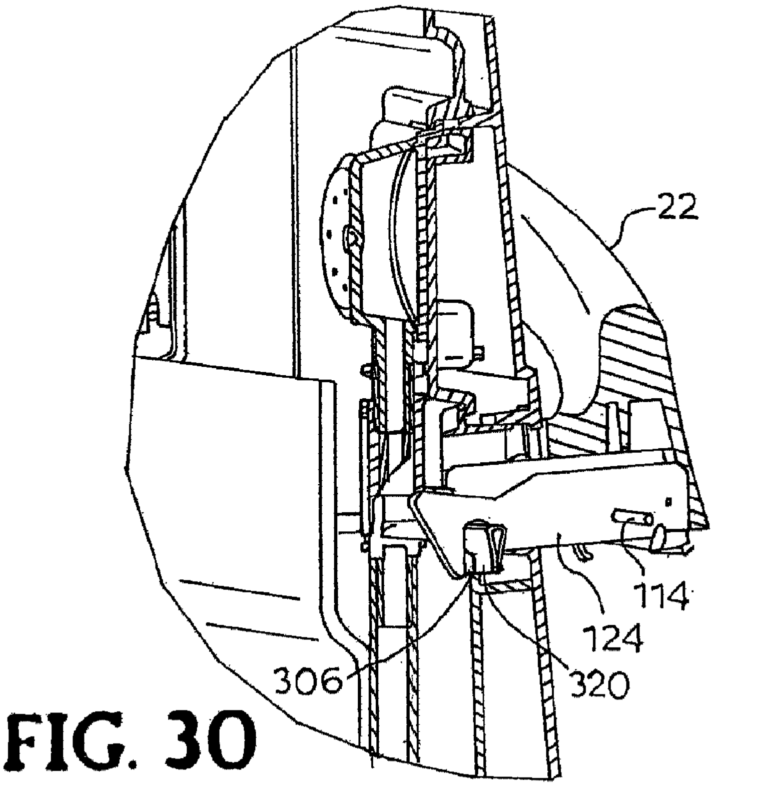
FIG. 30 is an isometric diagrammatic sectional view of the tray assembly, handle, pivotal latch and pivotal fork in a non-activated position.
Figure 31:
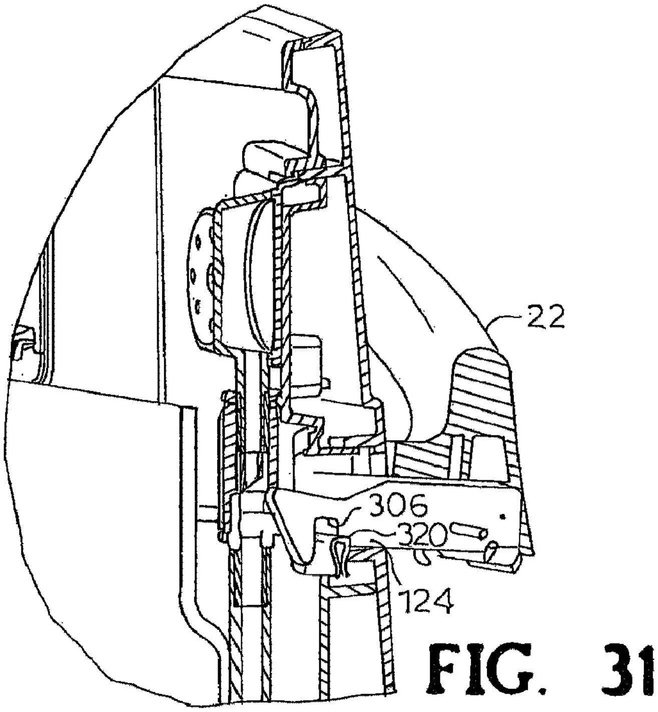
FIG. 31 is an isometric view similar to that shown in FIG. 30 but with the handle, pivotal fork and pivotal latch partially rotated.
Figure 32:
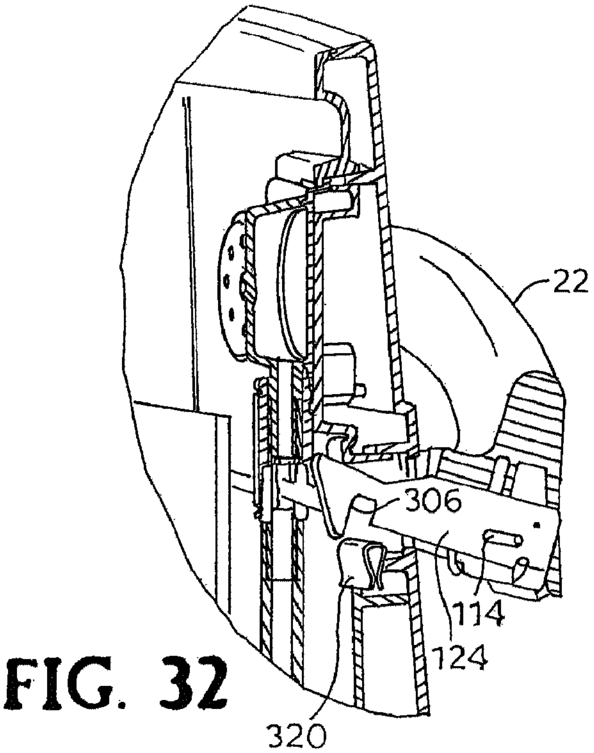
FIG. 32 is an isometric view similar to that shown in FIGS. 30 and 31 and with the handle, the pivotal latch and the pivotal fork fully rotated.
Figure 33:
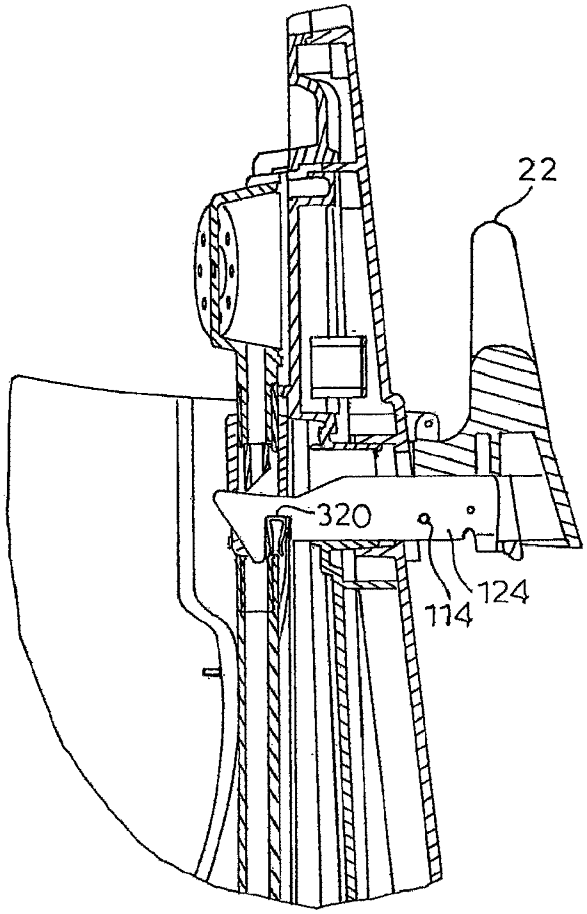
FIG. 33 is a diagrammatic section view showing the pivotal latch and the latch clip in engagement.
Figure 34:
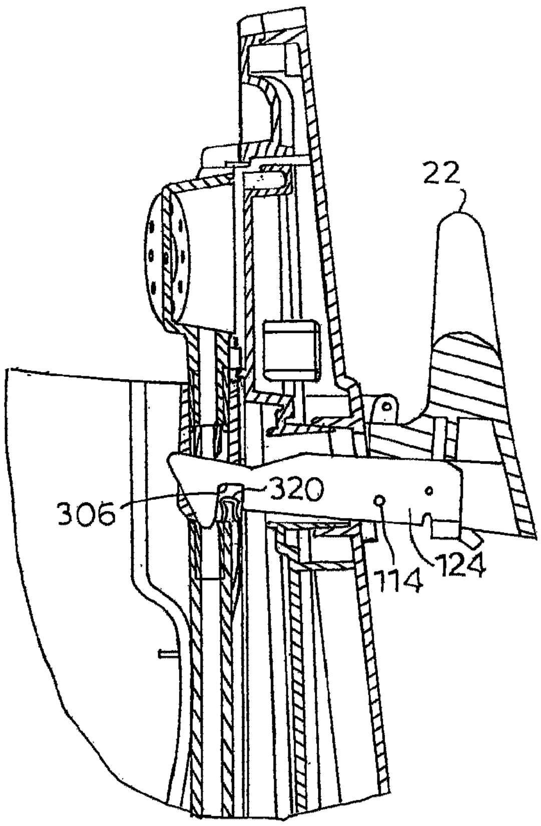
FIG. 34 is a sectional view similar to that shown in FIG. 33 but with only the pivotal latch partially rotated.
Figure 35:
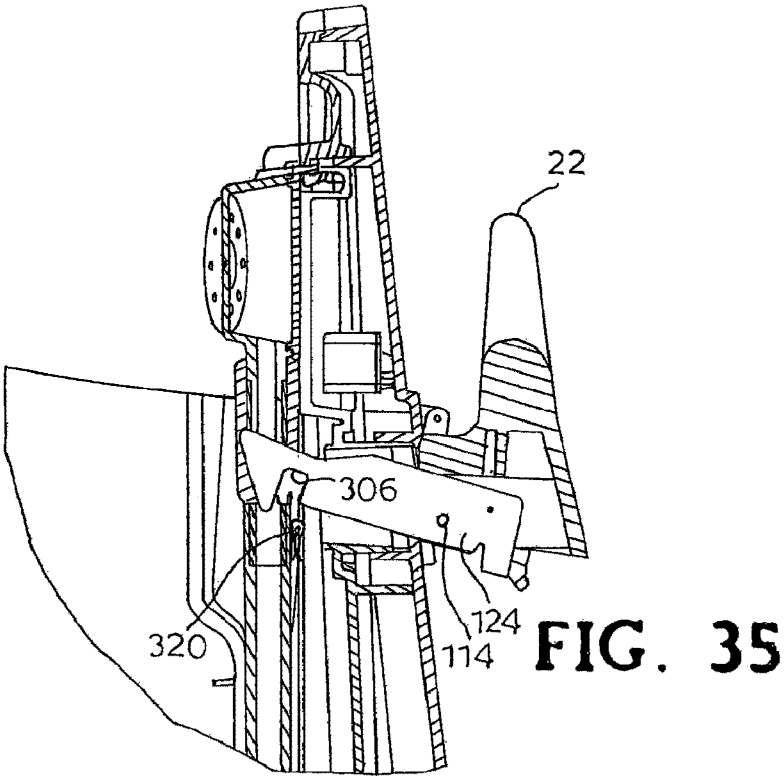
FIG. 35 is a sectional view similar to that shown in FIGS. 33 and 34 and with the pivotal latch fully rotated.
Figure 36:
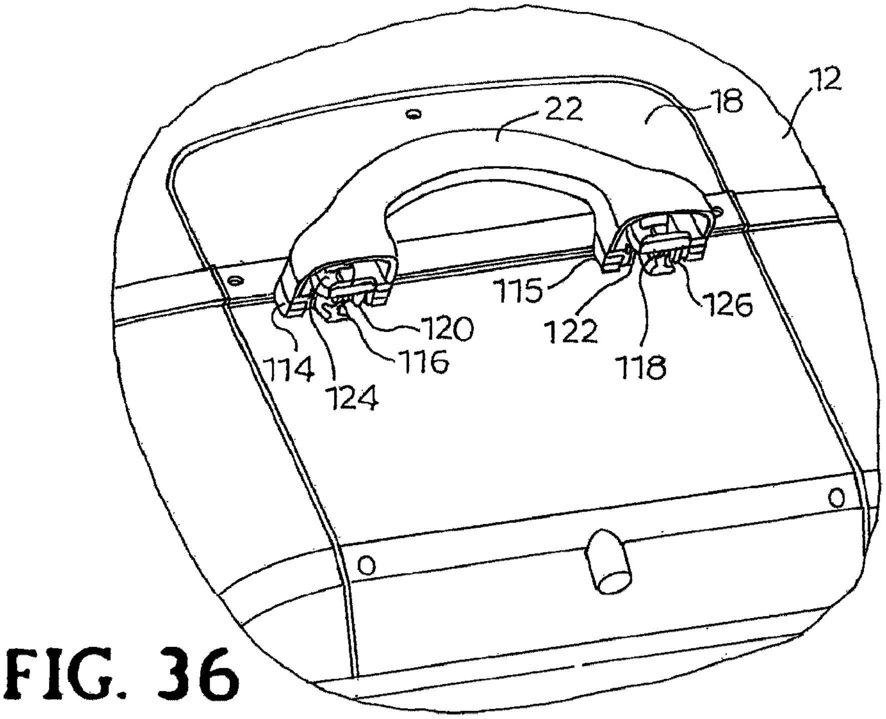
FIG. 36 is an upward looking isometric view of the tray assembly, the handle, the pivotal forks, the pivotal latches and a pair of torsion springs.

When the handle 22 pivots as shown progressively in FIGS. 30-32, the latch head slot 306 is moved out of engagement with the clip 320 and thus, the housing, so as to allow the tray assembly to move from its vertical closed position to its horizontal open position. Simultaneously, the pivotal forks are also rotated causing the membranes to be punctured and thereby start the flow of eye wash solution through the nozzles when the nozzles reach a predetermined elevation relative to the elevation of the bag assemblies. It should be noted that the pivotal latches are constructed to rotate either with the handle and thereby with the pivotal forks, or the pivotal latches may be rotated independently when the wing tabs 308 are depressed. This movement is shown progressively in FIGS. 33-35. Using the wing tabs allows the tray assembly to be opened for inspection of the bag assemblies, if desired, without pivoting the handle and piercing the membranes. Thus, the eye wash solution remains in a sealed undisturbed condition. Once the inspection is completed, the tray assembly may be closed. The torsion springs 116, 118 ensure that the pivotal latches are biased back into engagement with the clips mounted to the housing. The assembled arrangement of the handle 22, the pivotal forks 120, 122, the pivotal latches 124, 126 and the torsion springs 116, 118 are shown in more detail in FIG. 36.

Figure 37:
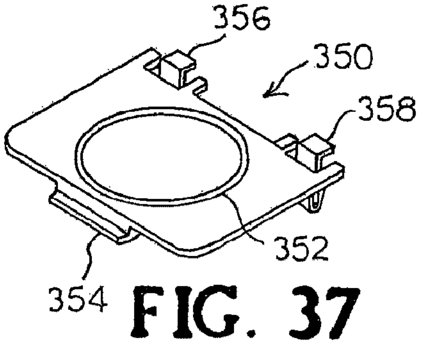
FIG. 37 is a front isometric view of a nozzle base.
Figure 38:
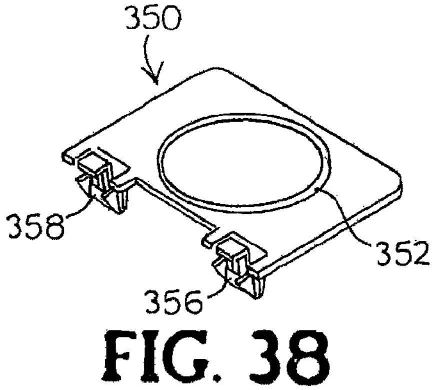
FIG. 38 is a rear isometric view of the nozzle base.
Figure 39:
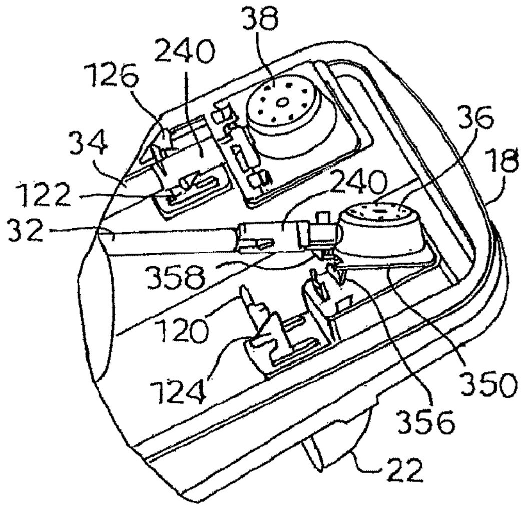
FIG. 39 is a diagrammatic elevation view of the nozzle and hose being installed on the tray assembly.

Referring now to FIGS. 37 and 38, there is illustrated a nozzle base 350 having a circular ridge 352 for engaging the lower edge 234 of the cup portion 230 of one of the nozzles 36, 38. The nozzle base includes at a forward end an engagement tab 354 and at a rearward end a pair of snap arms 356, 358. After the nozzles are engaged with the nozzle bases, the nozzle bases may be inserted on the nozzle pads 150, 152, FIG. 12, and by having the engagement tabs 354 received by the elongated slots 154, 160 of the inner tray part 110 and then pushing the snap arms 356, 358 into the smaller slots 156, 158 and 162, 164. This may be visualized by reference to FIG. 39.

Figure 40:
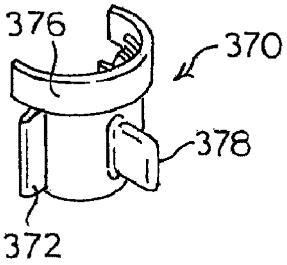
FIG. 40 is a front isometric view of a retainer clip.
Figure 41:
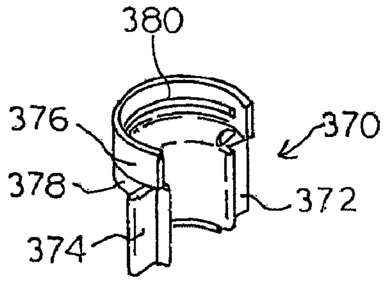
FIG. 41 is a rear isometric view of the retainer clip.
Figure 43:
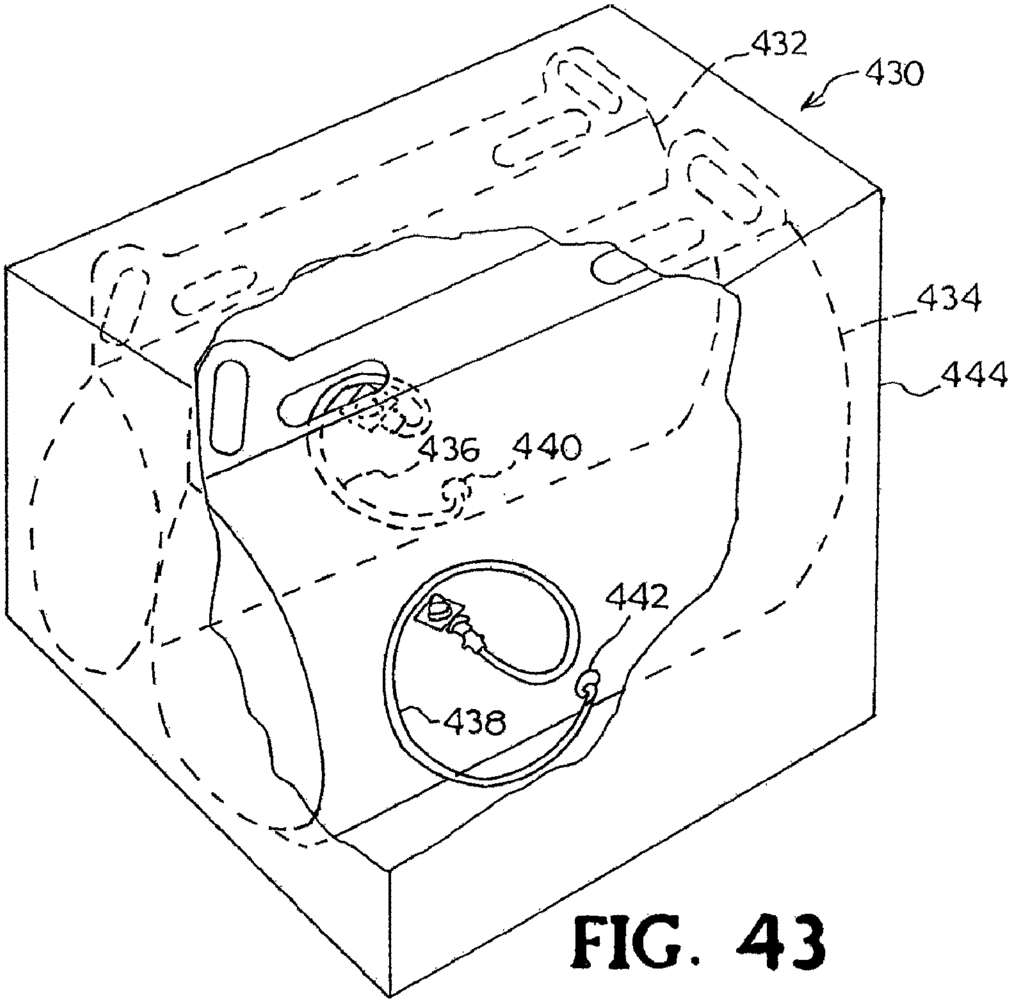
FIG. 43 is a diagrammatic, partially broken-away, isometric view of a kit containing two bag assemblies, two hoses and two nozzles in a shipping container.
Figure 44:
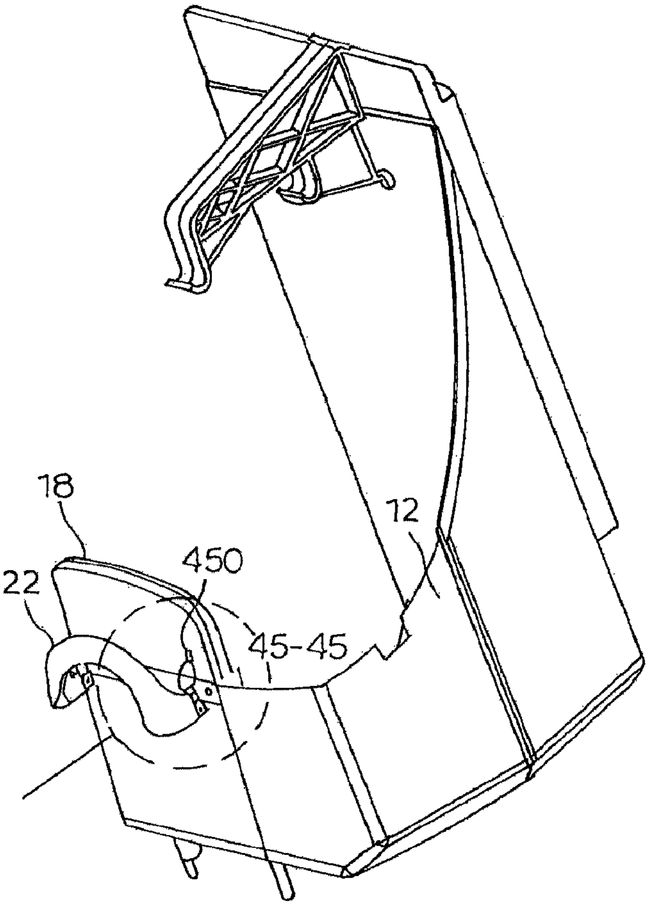
FIG. 44 is a partial isometric view illustrating the handle and a security seal.
Figure 45:
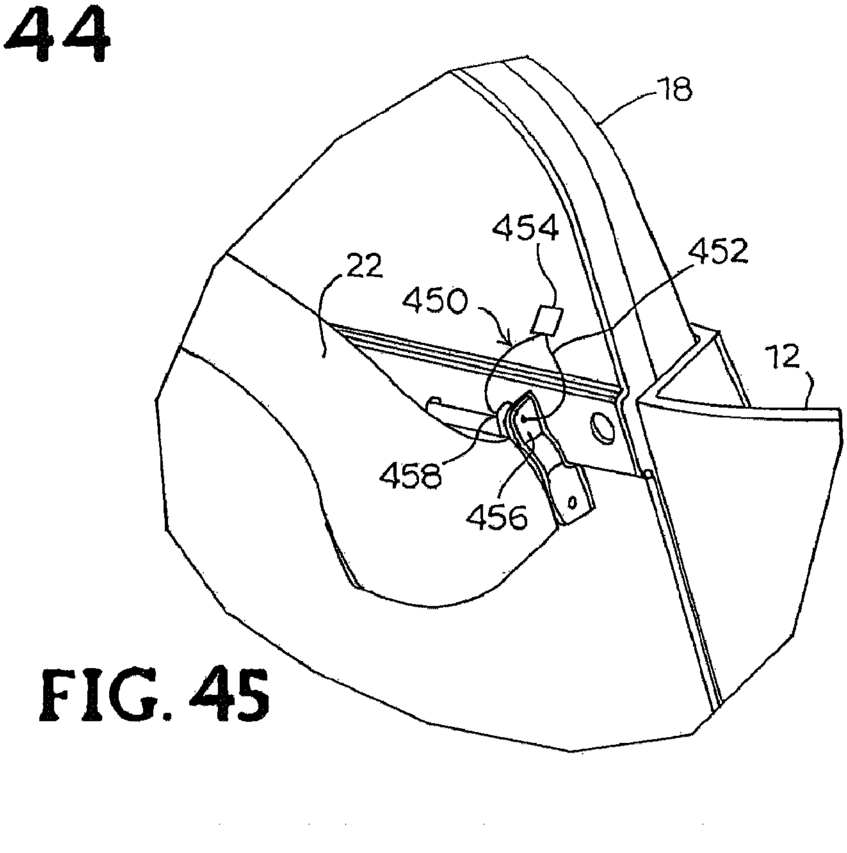
FIG. 45 is a view taken within circle 45-45 of FIG. 44.
Figure 46:
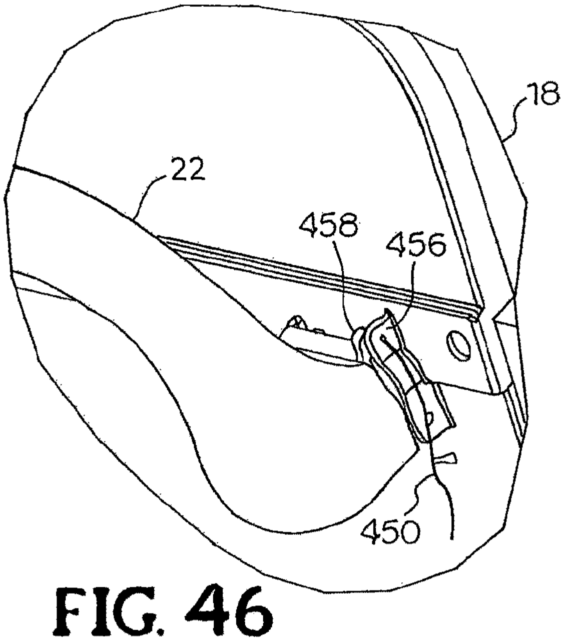
FIG. 46 is a view similar to that of FIG. 45 but with a broken seal.
Figure 47:
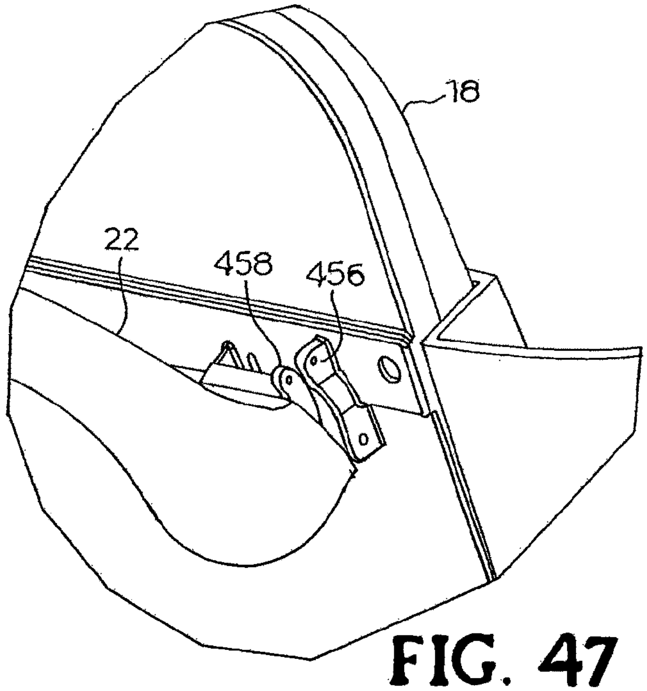
FIG. 47 is a view similar to that of FIGS. 45 and 46 but with a pivoted handle and a fallen-away seal.
Figure 48:
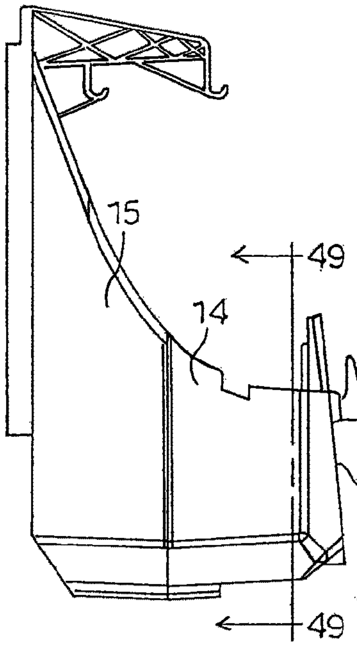
FIG. 48 is a side elevation view of a portion of the eye wash system with the tray in a closed position.
Figure 49:
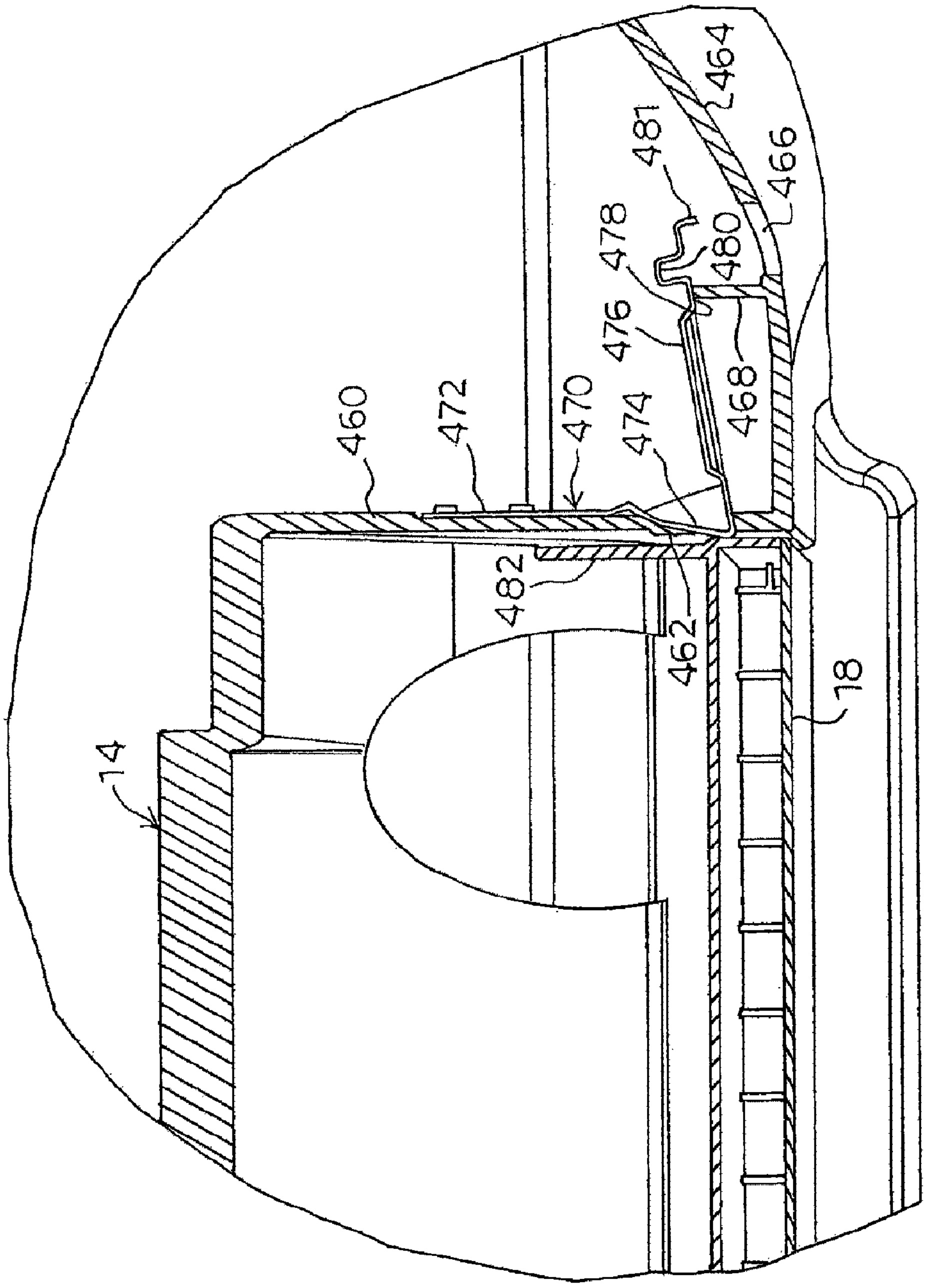
FIG. 49 is a view taken along line 49-49 of FIG. 48.
Figure 51:
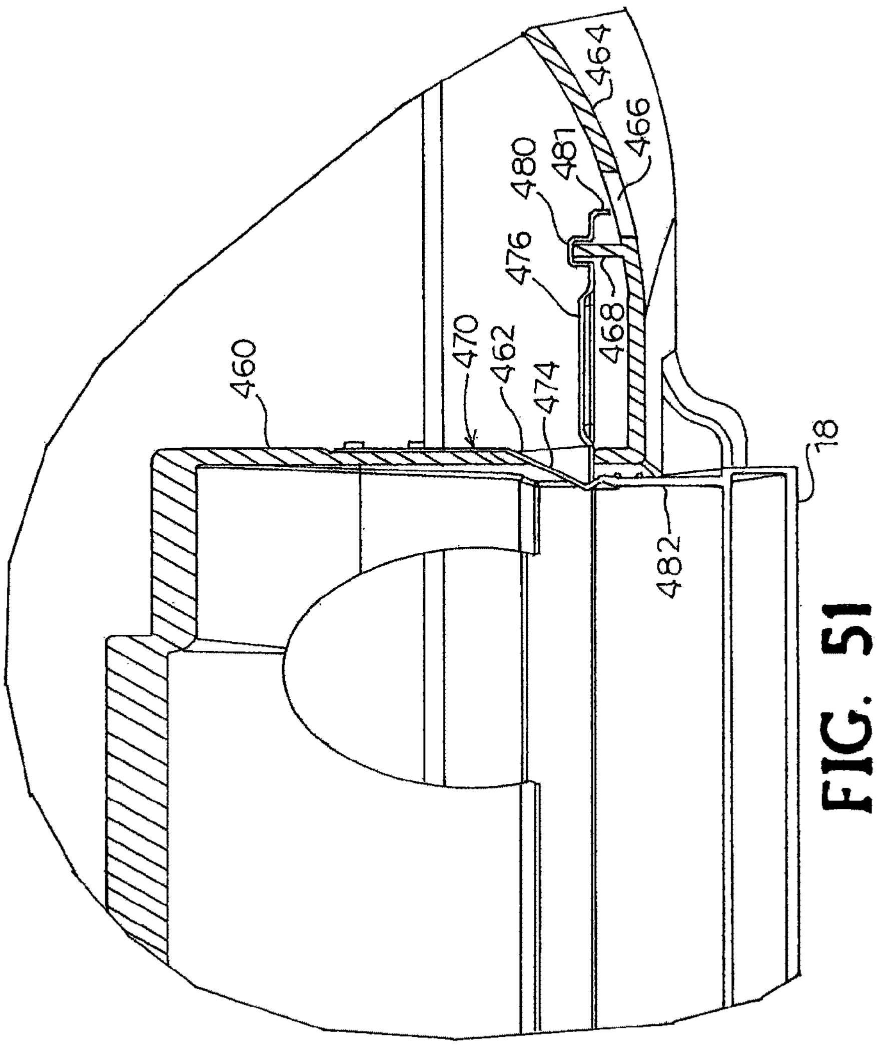
FIG. 51 is a view taken along line 51-51 of FIG. 50.
Figure 50:
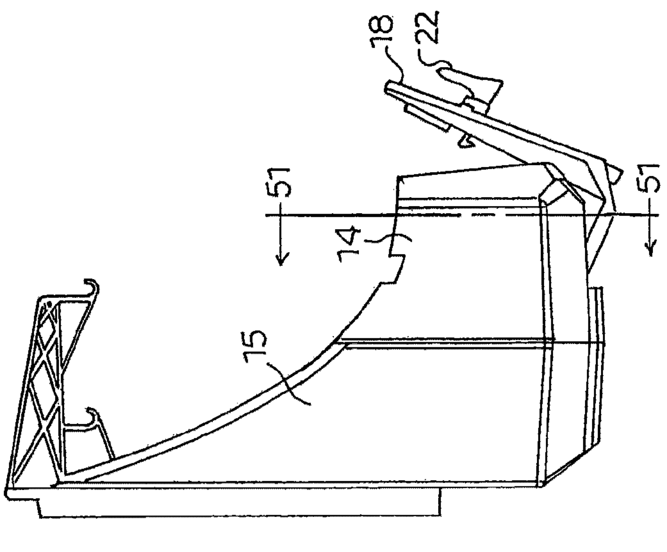
FIG. 50 is a side elevation view of a portion of the eye wash system with the tray in a partially open position.
Figure 52:
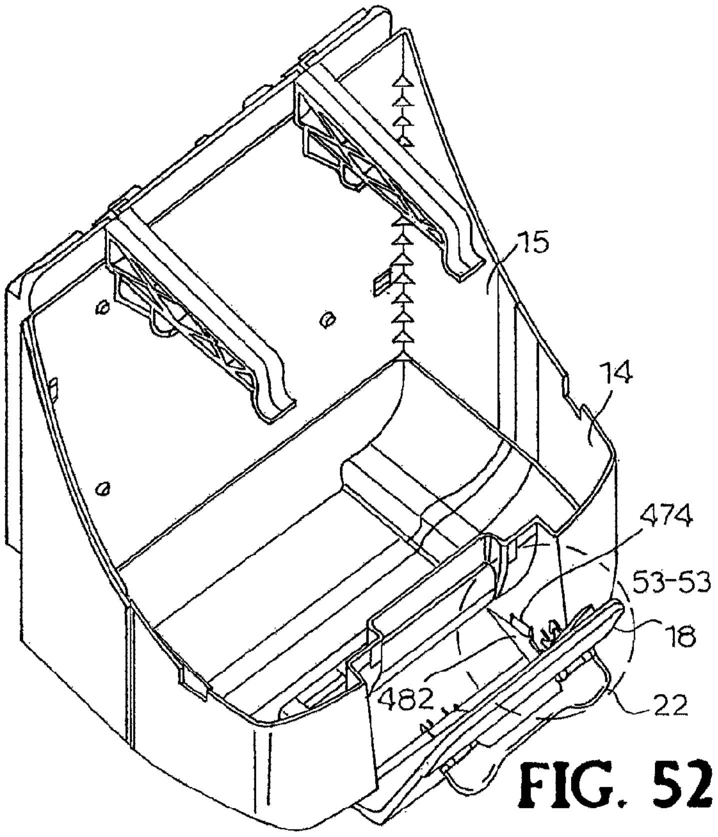
FIG. 52 is a downward looking isometric view of the eye wash system as shown in FIG. 50.
Figure 53:
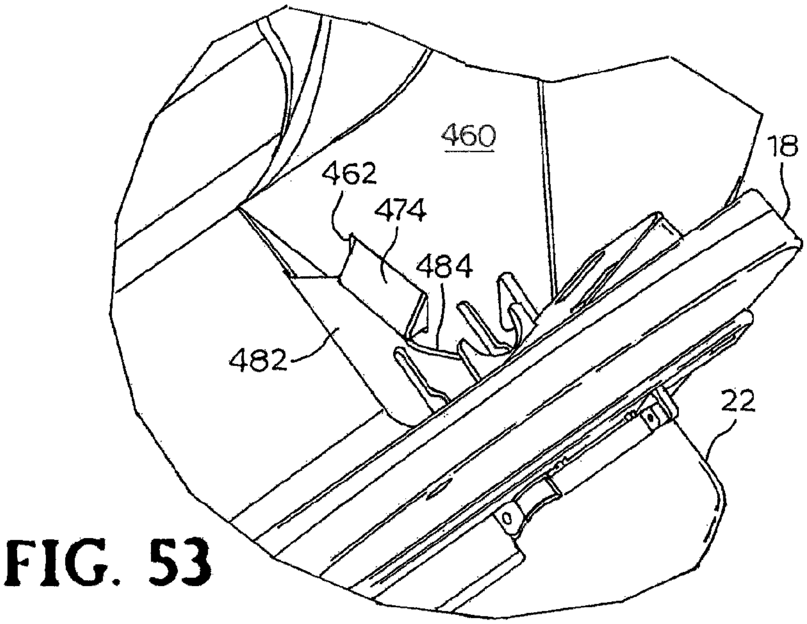
FIG. 53 is a view taken within the circle 53-53 of FIG. 52.
Figure 54:
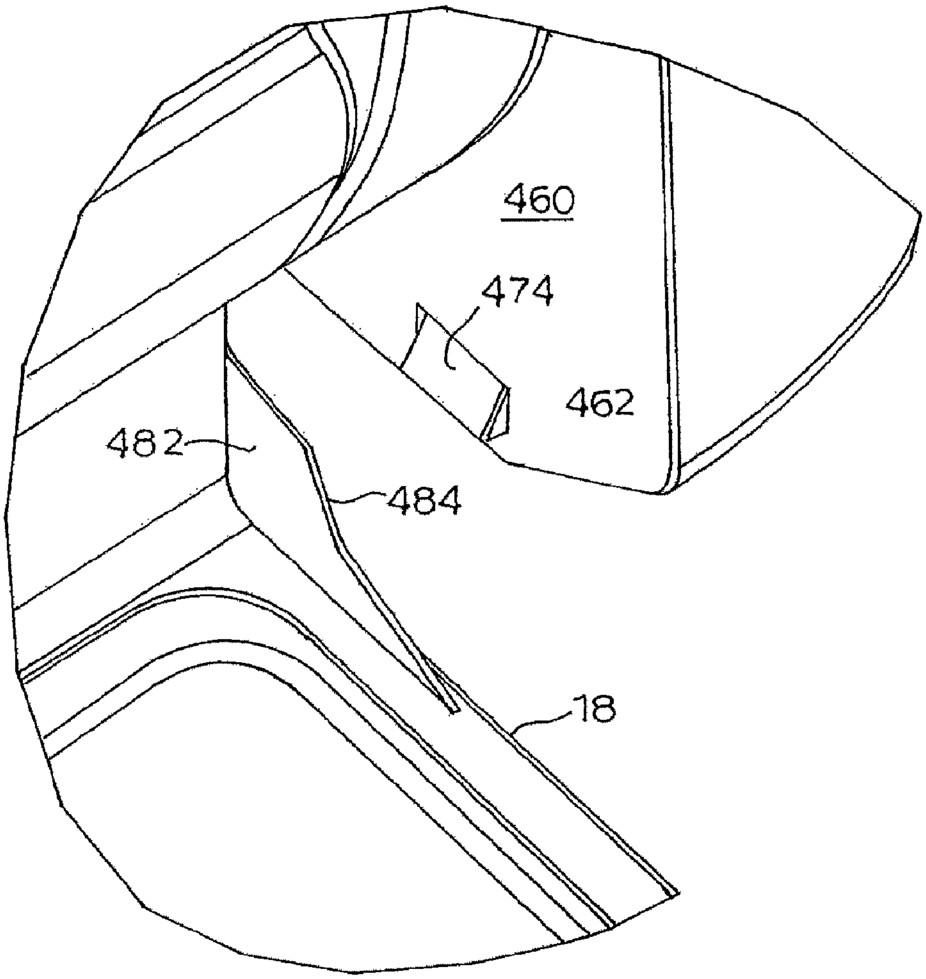
FIG. 54 is a view similar to that of FIG. 53 but with the tray fully open.

A retainer clip 370 is illustrated in FIGS. 40, and 41. The retainer clip is structured to fit around the nozzle stem 236. FIG. 14, and thereby blocks any sliding advancement downstream by the connector sleeve 240 towards the nozzle cup 230. The retainer clip has an open cylindrical shape with two oppositely extending abutment wings 372, 374. The retainer clip includes a collar 376 at one end and a dorsal tab 378. Interior of the retainer clip is an arcuate projection 380 which is designed to engage a corresponding groove 382, FIG. 14, in the stem 236 of the nozzle.

Figure 29:
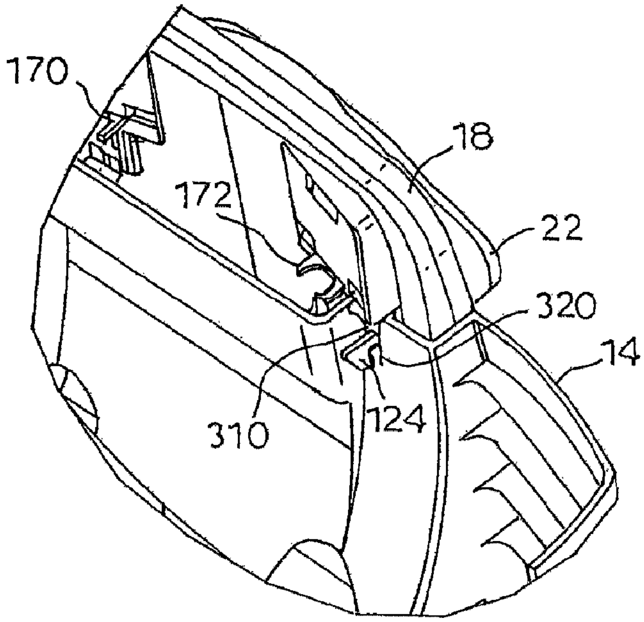
FIG. 29 is an isometric view of the tray assembly, the pivotal latch, the latch clip and the housing front part.

The abutment wings 372, 374 are designed to engage the prongs 170, 172, FIGS. 11 and 29, so as to automatically disengage the retainer clip 370 from the nozzle stem when the nozzle and hose are engaged with the tray 18.

The retainer clips are used only during transit of the bag assemblies 28, 30 to ensure that there is no inadvertent puncture of the membranes. However, when the bag assemblies and attached hoses and nozzles are installed in the housing and to the tray, the retainer clips are removed so that the system becomes fully operational and ready for use.

Figure 42:
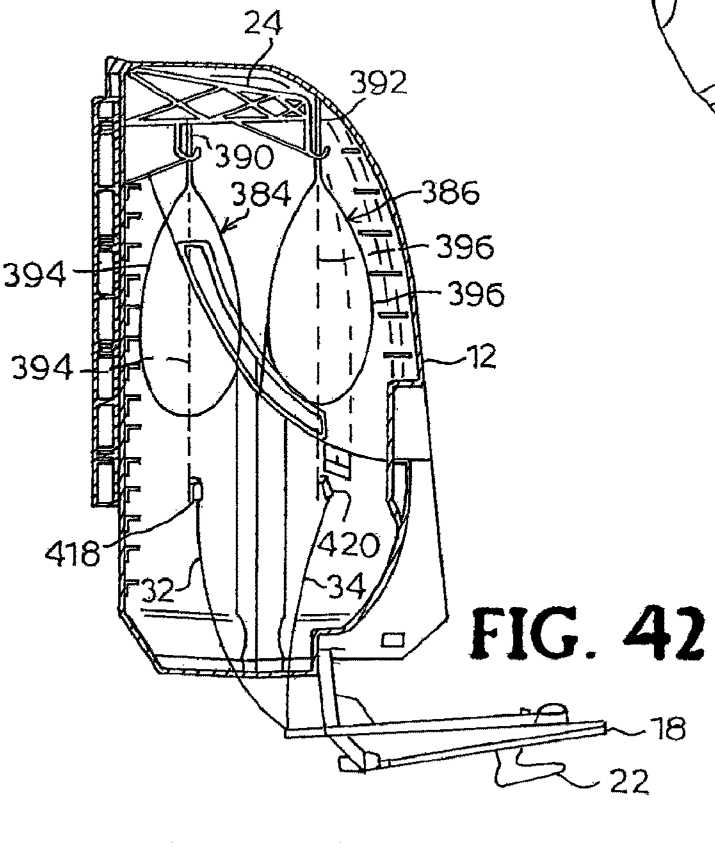
FIG. 42 is a diagrammatic sectional view of the emergency eye wash system illustrating the tray assembly in a lowered, activated position, and bag assemblies in solid line when full and in broken line when emptied.

The two bag assemblies 28 and 30 are illustrated in FIGS. 4 and 42, and will be described in detail here. Each bag assembly includes one storage bag 384, 386 having a structural top of rigid plastic 390, 392 and lower resilient sheets 394, 396. Each of the tops 390, 392 include a pair of outer diagonally oriented slots 400, 402 and 404, 406 and an inner pair of generally horizontally oriented slots 410, 412 and 414, 416. The outer slots allow personnel performing an installation to grip each bag to facilitate lifting the bag from a protective package to the hanger brackets 24, 26. The bags are hung on the brackets by using the inner slots. The housing provides clearance between itself and the bags when the bags are full and there is a clearance between the full bags as well. Each bag also includes a spout 418, 420 to which the hoses 32, 34 are attached. It is noted that there is no mechanical or other external device used to apply pressure to the bags.

The resilient sheets, preferably, are constructed from a polyolefin film such as medical grade COVELLE 1200 Clear brand polyolefin film which is commercially available from The Dow Chemical Company, having a thickness, preferably, in a range of about 10 to about 20 mils (0.010 inches to 0.020 inches ), most preferably about 14 mils (0.014inches ). Another example of a poyolefin film material suitable for forming the resilient sheets herein is medical grade CRYOVAC M312 brand film, having a thickness of about 7.5 mils (0.0075 inches ), which is commercially available from Cryovac Inc. Other suitable resilient, polymeric film materials suitable for use herein include medical grade polyvinyl chloride (PVC) films, ethylene vinyl acetate (EVA) films and other similar polymeric materials.

The polymeric films to be used herein are resilient, having memory, and provide a continuing pressure on the eye wash solution inside the bag. In this regard, the COVELLE 1200 Clear brand film is known to exhibit a tensile modulus, 2% secant, of 5800 psi when tested in accordance with the ASTMD 882 test procedure. The CRYOVAC M312 brand film has a modulus of elasticity value of about 12,800 psi.

When empty, the combined height of a bag 384, 386 including a bag 390, 392 is in a range of about fifteen to about twenty inches, preferably about nineteen inches high. The width of the bags is in a range of about eighteen to about twenty-five inches, preferably about twenty-one inches.

The bags are hung in the housing on brackets in a manner such that the spouts on the bags are at a level in a range of about eight to about fifteen inches above the nozzles and, preferably, about twelve and half inches, when the bags are full, and about ten and a half inches, when the bags are empty. This positioning is intended to ensure a generally constant flow of solution from an individual bag at a rate of no less than about three quarters of a liter per minute during a fifteen minute period when a double bag arrangement is employed in an eyewash system. The double bag arrangement will result in a total rate of flow of one and a half liters per minute, with three quarters of a liter per minute from each of the two bags. The preferred volume of solution in each bag is about fourteen liters, although the range of volume may vary from a minimum of about eleven and a quarter liters up to about seventeen liters. Since the arrangement is a two bag system, the total minimum volume of the sterile solution will be two and a half liters.

It is desirable that the bags will be substantially evacuated after activation of the system. The design of the bags disclosed herein meet this criterion and, also, such design eliminates any need for external pressure to be applied to the bags in order for the solution to be dispersed at the desired flow rate contrary to prior art eye wash devices. The bags of the present invention are illustrated diagrammatically in FIG. 42 in solid line to represent a full condition and in broken line when the bags are in an empty condition.

It is noted that the housing 12 is independent of the bags, hoses and nozzles, in that the bags, hoses and nozzles are replaceable and thus may be sold as a kit. Optimally the two bags contain approximately twenty-eight liters of sterile, sealed eye wash solution and the bags, hoses and nozzles are part of a sealed sub-system for maintaining the solution in a sterile condition. After the emergency eye wash system is used, the empty bags and attached hoses and nozzles are removed and sent for disposal. A new kit 430 of two bag assemblies 432, 434 with sterile solution, hoses 436, 438 and nozzles 440, 442 packaged in a disposable, corrugated box 444 for shipment is acquired, and the new kit is installed in the housing simply by lifting the bag assemblies so as to the engage the hanger brackets, threading the nozzle and hoses through the openings 92, 94 in the front housing part 14, FIG. 5, and then snapping the nozzles onto the nozzle pads 150, 152 of the tray assembly 18. The engagement of the nozzles with the nozzle pads causes the retainer clips 370 to be pried off of the hoses thereby placing the emergency eye wash system into operative mode. Thereafter, the tray assembly may be moved from the horizontal open position to the vertical closed position without touching the handle 22 so that the system is ready for use.

A preferred eye wash fluid is a solution of buffered isotonic saline solution, having a shelf life of at least two years. However, it is to be noted that a non-sterile solution may be used herein.

Referring now to FIGS. 44-47, the eye wash system includes a tray security seal in the form of a date-coded tag 450. The tag includes a frangible wire 452 and a seal tab 454. The wire fits through a hole in a flange 456 integral with the tray and an alignable hole in a tab 458 integral with the handle 22. Rotating the handle shears the wire.

The function of the tag 450 is to indicate that the system is operable when the seal is secured and unbroken and to indicate that the system may not function or has been tampered with when the seal is broken or missing. The tag also indicates an expiration date for the eyewash solution and provides facilitated inspection.

Inspection of the system can also be performed by viewing the solution containing bags through the inspection windows. Still other inspection methods include the removal of the lid without any movement of the tray, or lowering the tray without moving the handle.

Another security feature of the system may be understood by reference to FIGS. 48-54. The front housing part 14 includes a lateral side wall 460 with an opening 462 and a bottom wall 464, and it also includes an opening 466. Adjacent the opening and integral with the bottom wall is an upstanding flange 468. Attached to the side wall 460 is an L-shaped spring metal latch 470 having a vertically extending arm portion 472 staked to the side wall 460 and an abutment portion 474 which extends through the side wall opening 462. The spring latch 470 also includes a horizontally extending arm portion 476 having a flange abutment surface 478, a flange engagement groove 480 and an unlocking tab 481. As shown best in FIG. 49, when the tray is in its vertical closed position, a side flange 482 integral with the tray is positioned adjacent the side wall opening 462 and bears against the abutment portion 474 of the spring latch. When in this position the horizontal arm portion 476 is biased to the right in the disposition shown in FIG. 49, so that the upstanding flange 468 biases the side extending arm portion 476 upwardly by bearing against the flange abutment surface 478. However, as soon as the tray is pivoted toward its horizontal open position, the tray side flange 482 moves away from the abutment portion 474 of the spring latch 470 and the abutment portion springs leftward into the side wall opening 462. This allows the horizontally extending arm portion 476 to slide leftwardly causing the groove 480 of the arm portion to spring into engagement with the upstanding flange 468. When this occurs, there is an interference fit between the groove 480 and the flange 468. This results in the placement of the abutment portion 474 of the spring latch into a blocking position relative to the tray flange 482 so that the tray cannot return to its closed vertical position without an action by someone to reset the spring latch. Without the reset, a top edge 484 of the flange 482 will come into contact with the abutment portion 474 of the spring latch and prevent any further upward movement.

The spring latch may be reset by an operator inserting her finger or a tool through the bottom wall opening 466 to push the tab 481 upwardly. This causes a rightward movement of the horizontal arm portion 476 and the abutment portion 474. At the same time, if the tray is lifted toward the vertical, closed position, the tray flange 482 will again move into a position to bias the arm portion 476 and the abutment portion 474 to the configuration shown in FIG. 49. The operation of the spring latch feature should ensure that the tray is not closed inadvertently after use.

It is now appreciated that the emergency eye wash system disclosed here is compact, relatively simple in construction and relatively inexpensive. Also of importance is that the system is reliable.

The above description sets forth in detail the preferred embodiment of the present invention. Other examples, embodiments, modifications and variations will, under both the literal claim language and the doctrine of equivalents, come within the scope of the invention defined by the appended claims. For example, mere modification of various physical features of the herein disclosed system including such features as bag size, bag volume, the number of bags, the bag hang height above the elevation of the pair of nozzles, the bag material, the hose diameter, the hose length and/or the shape, size or number of holes of the nozzle are all considered to fall within the literal language of the following claims. Furthermore, changing the shape of the housing, or the brackets or the tray will still be considered to be equivalent structures. In addition, they will come within the literal language of the claims. Still other alternatives will also be equivalent as will many new technologies. There is no desire or intention here to limit in any way the application of the doctrine of equivalents nor to limit or restrict the scope of the invention.

The invention claimed is:

1. A kit for use in storing and dispensing eye wash fluid in an eye wash station comprising:

an eye wash fluid storage element; and a movable structure;

a flexible conduit in fluid connection with the storage element and defining a flow path for dispensing the eye wash fluid from the storage element, the flow path being closed to fluid flow when the movable structure is in a first position and being opened by movement of the movable structure to a second position to enable the eye wash fluid to flow from the storage element through the flow path;

a membrane directly connected to the conduit, the membrane being dimensioned and configured for closing the flow path; and a membrane piercing element disposed for engagement with the membrane upon movement of the movable structure from the first position where the membrane piercing element is not in engagement with the membrane to the second position where the membrane piercing element is in engagement with the membrane;

wherein the membrane piercing element is directly connected to a nozzle;

a removable retainer clip maintains the movable structure in a fixed position prior to use;

the movable structure includes a handle, the handle being dimensioned and configured during use to start the eye wash fluid flowing to the nozzle upon movement of the handle;

the storage element is a bag assembly;

the bag assembly includes at least one storage bag;

the storage bag has a structural top and lower resilient sheets, the structural top being made of rigid plastic, the structural top including a pair of outer slots and a pair of inner slots, the outer slots being adjacent the ends of the structural top, and the inner slots being spaced inwardly from the outer slots, the outer and inner slots being dimensioned and configured to facilitate gripping and lifting the bag.

2. The kit as claimed in claim 1 including:

a spray nozzle connected to the conduit.

3. The kit as claimed in claim 1 wherein:

the membrane piercing element is structured and dimensioned to puncture the membrane and to move the membrane out of a fluid interfering position and to maintain the membrane in a non-interfering position enabling the eye wash fluid to flow upon movement of the conduit.

4. The kit as claimed in claim 1 wherein:

the membrane piercing element is cylindrically shaped with a sharp edge.

5. The kit as claimed in claim 1 wherein:

the storage bag includes a spout connected to the movable structure.

6. The kit as claimed in claim 1 wherein:

the resilient sheets are made of a polyolefin film having a thickness of about 0.014 inches.

7. The kit as claimed in claim 6 wherein:

the polyolefin film provides a pressure on the eye wash fluid inside the bag to help enable a generally constant flow of fluid from the bag during use at a rate of about one and a half liters per minute during a fifteen minute period and to help cause the fluid to be substantially evacuated from the bag.

8. The kit as claimed in claim 1 wherein:

the kit includes a plurality of storage bags;

the storage bags and tops are about nineteen inches high and twenty-one inches wide when empty.

9. The kit as claimed in claim 1 wherein:

the kit includes a plurality of storage bags;

the storage bags contain about twenty-two and a half liters of sterile, sealed eye wash solution.

* * * * *